United States Patent
Brennan et al.

(10) Patent No.: US 7,896,650 B2
(45) Date of Patent: Mar. 1, 2011

(54) DENTAL COMPOSITIONS INCLUDING RADIATION-TO-HEAT CONVERTERS, AND THE USE THEREOF

(75) Inventors: Joan V. Brennan, Sierra Madre, CA (US); Rajdeep S. Kalgutkar, Woodbury, MN (US); Mario A. Perez, Burnsville, MN (US); Wayne S. Mahoney, St. Paul, MN (US); Peter A. Stark, Cottage Grove, MN (US); Joel D. Oxman, Minneapolis, MN (US); Darrell S. James, Covina, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 677 days.

(21) Appl. No.: 11/275,243

(22) Filed: Dec. 20, 2005

(65) Prior Publication Data

US 2007/0141524 A1  Jun. 21, 2007

(51) Int. Cl.
*A61C 15/00* (2006.01)
*A61F 2/00* (2006.01)

(52) U.S. Cl. .................... 433/215; 523/115
(58) Field of Classification Search .......... 433/215; 523/115–118
See application file for complete search history.

(56) References Cited

U.S. PATENT DOCUMENTS

| | | |
|---|---|---|
| 3,018,262 A | 1/1962 | Schroeder |
| 3,775,113 A | 11/1973 | Bonham et al. |
| 3,779,778 A | 12/1973 | Smith et al. |
| 3,954,475 A | 5/1976 | Bonham et al. |
| 3,975,422 A | 8/1976 | Buck |
| 4,094,068 A | 6/1978 | Schinhammer |
| 4,180,911 A | 1/1980 | Bullock |
| 4,200,980 A * | 5/1980 | Johnston .......... 433/8 |
| 4,259,075 A | 3/1981 | Yamauchi et al. |
| 4,298,738 A | 11/1981 | Lechtken et al. |
| 4,324,744 A | 4/1982 | Lechtken et al. |
| 4,329,384 A | 5/1982 | Vesley et al. |
| 4,330,570 A | 5/1982 | Giuliani et al. |
| 4,356,296 A | 10/1982 | Griffith et al. |
| 4,385,109 A | 5/1983 | Lechtken et al. |
| 4,435,160 A * | 3/1984 | Randklev .......... 433/9 |

(Continued)

FOREIGN PATENT DOCUMENTS

DE  3836619  5/1990

(Continued)

OTHER PUBLICATIONS

Rickabaugh J, Marangoni R, McCaffrey K. Ceramic bracket debonding with the carbon dioxide laser. American Journal of Orthodontics and Dentofacial Orthopedics 1996; 110:388-393.*

(Continued)

*Primary Examiner*—Cris L Rodriguez
*Assistant Examiner*—Heidi M Eide
(74) *Attorney, Agent, or Firm*—Philip P. Soo

(57) ABSTRACT

Hardenable and hardened dental compositions that include radiation-to-heat converters, and articles including such hardenable and hardened compositions, are provided. Upon irradiating, the hardened compositions increase in temperature, which can be useful for reducing the bond strengths of orthodontic appliances adhered to tooth structures with the hardened compositions.

12 Claims, 5 Drawing Sheets

U.S. PATENT DOCUMENTS

| | | |
|---|---|---|
| 4,455,138 A * | 6/1984 | Sheridan ............................ 433/3 |
| 4,457,818 A | 7/1984 | Denyer et al. |
| 4,499,251 A | 2/1985 | Omura et al. |
| 4,500,657 A | 2/1985 | Kumar |
| 4,503,169 A | 3/1985 | Randklev |
| 4,537,940 A | 8/1985 | Omura et al. |
| 4,539,382 A | 9/1985 | Omura et al. |
| 4,554,336 A | 11/1985 | Kidd et al. |
| 4,590,145 A | 5/1986 | Itoh et al. |
| 4,642,126 A | 2/1987 | Zador et al. |
| 4,648,843 A | 3/1987 | Mitra |
| 4,652,274 A | 3/1987 | Boettcher et al. |
| 4,665,217 A | 5/1987 | Reiners et al. |
| 4,673,354 A | 6/1987 | Culler |
| 4,695,251 A | 9/1987 | Randklev |
| 4,710,523 A | 12/1987 | Lechtken et al. |
| 4,737,593 A | 4/1988 | Ellrich et al. |
| 4,749,352 A | 6/1988 | Nicholson |
| 4,752,338 A | 6/1988 | Reiners et al. |
| 4,824,366 A | 4/1989 | Hohmann et al. |
| 4,872,936 A | 10/1989 | Engelbrecht |
| 4,904,183 A | 2/1990 | Hannan et al. |
| 4,920,188 A | 4/1990 | Sakashita et al. |
| 4,948,366 A | 8/1990 | Horn et al. |
| 4,950,157 A | 8/1990 | Cleary |
| 4,952,142 A | 8/1990 | Nicholson |
| 4,978,007 A | 12/1990 | Jacobs et al. |
| 5,008,304 A | 4/1991 | Kmentt |
| 5,011,410 A | 4/1991 | Culler et al. |
| 5,015,180 A | 5/1991 | Randklev |
| 5,026,902 A | 6/1991 | Fock et al. |
| 5,035,612 A | 7/1991 | Martin et al. |
| 5,037,861 A | 8/1991 | Crivello et al. |
| 5,040,975 A | 8/1991 | Ettwein et al. |
| 5,062,793 A | 11/1991 | Cleary et al. |
| 5,063,257 A | 11/1991 | Akahane et al. |
| 5,066,231 A | 11/1991 | Oxman et al. |
| 5,076,844 A | 12/1991 | Fock et al. |
| 5,089,374 A | 2/1992 | Saeva |
| 5,098,288 A | 3/1992 | Kesling |
| 5,106,302 A | 4/1992 | Farzin-Nia et al. |
| 5,108,285 A | 4/1992 | Tuneberg |
| 5,110,290 A | 5/1992 | Wong |
| 5,122,061 A | 6/1992 | Wakumoto et al. |
| 5,130,347 A | 7/1992 | Mitra |
| 5,141,969 A | 8/1992 | Saeva et al. |
| 5,154,762 A | 10/1992 | Mitra et al. |
| 5,172,809 A | 12/1992 | Jacobs et al. |
| 5,205,734 A | 4/1993 | Marangoni et al. |
| 5,219,283 A | 6/1993 | Farzin-Nia et al. |
| 5,227,413 A | 7/1993 | Mitra |
| 5,256,062 A | 10/1993 | Griott |
| 5,263,859 A | 11/1993 | Kesling |
| 5,269,680 A | 12/1993 | Kawaguchi |
| 5,269,682 A | 12/1993 | Kesling |
| 5,295,824 A * | 3/1994 | Wong ............................ 433/9 |
| 5,320,532 A | 6/1994 | Farzin-Nia et al. |
| 5,328,363 A | 7/1994 | Chester et al. |
| 5,354,199 A | 10/1994 | Jacobs et al. |
| 5,366,372 A | 11/1994 | Hansen et al. |
| 5,367,002 A | 11/1994 | Huang et al. |
| 5,393,362 A | 2/1995 | Culler |
| 5,403,188 A | 4/1995 | Oxman et al. |
| 5,415,544 A | 5/1995 | Oxman et al. |
| 5,439,379 A | 8/1995 | Hansen |
| 5,457,149 A | 10/1995 | Hall et al. |
| 5,501,727 A | 3/1996 | Wang et al. |
| 5,520,725 A | 5/1996 | Kato et al. |
| 5,525,648 A | 6/1996 | Aasen et al. |
| 5,530,038 A | 6/1996 | Yamamoto et al. |
| 5,545,676 A | 8/1996 | Palazzotto et al. |
| 5,554,664 A | 9/1996 | Lamanna et al. |
| 5,569,691 A | 10/1996 | Guggenberger et al. |
| 5,583,178 A | 12/1996 | Oxman et al. |
| 5,635,545 A | 6/1997 | Oxman et al. |
| 5,709,548 A | 1/1998 | Oxman et al. |
| 5,722,826 A | 3/1998 | Tuneberg et al. |
| 5,746,594 A | 5/1998 | Jordan et al. |
| 5,829,972 A | 11/1998 | Farzin-Nia |
| 5,856,373 A | 1/1999 | Kaisaki et al. |
| 5,859,089 A | 1/1999 | Qian |
| 5,871,360 A | 2/1999 | Kato |
| 5,925,715 A | 7/1999 | Mitra |
| 5,962,550 A | 10/1999 | Akahane et al. |
| 5,965,632 A | 10/1999 | Orlowski et al. |
| 6,030,606 A | 2/2000 | Holmes |
| 6,084,004 A | 7/2000 | Weinmann et al. |
| 6,089,861 A | 7/2000 | Kelly et al. |
| 6,090,867 A | 7/2000 | Starling, Jr. et al. |
| 6,121,362 A | 9/2000 | Wanek et al. |
| 6,127,449 A | 10/2000 | Bissinger et al. |
| 6,147,141 A | 11/2000 | Iyer et al. |
| 6,159,012 A | 12/2000 | Oxman et al. |
| 6,183,249 B1 | 2/2001 | Brennan et al. |
| 6,187,833 B1 | 2/2001 | Oxman et al. |
| 6,187,836 B1 | 2/2001 | Oxman et al. |
| 6,245,828 B1 | 6/2001 | Weinmann et al. |
| 6,251,963 B1 | 6/2001 | Köhler et al. |
| 6,282,013 B1 * | 8/2001 | Ostler et al. ............... 359/309 |
| 6,331,080 B1 | 12/2001 | Cole et al. |
| 6,331,343 B1 | 12/2001 | Perez et al. |
| 6,361,721 B1 | 3/2002 | Stern |
| 6,376,585 B1 * | 4/2002 | Schofalvi et al. ............ 524/195 |
| 6,387,981 B1 | 5/2002 | Zhang et al. |
| 6,395,124 B1 | 5/2002 | Oxman et al. |
| 6,395,801 B1 | 5/2002 | Bissinger et al. |
| 6,417,244 B1 | 7/2002 | Wellinghoff et al. |
| 6,444,725 B1 | 9/2002 | Trom et al. |
| 6,458,868 B1 | 10/2002 | Okada et al. |
| 6,465,541 B2 | 10/2002 | Bretscher et al. |
| 6,474,988 B1 | 11/2002 | Georgakis et al. |
| 6,506,816 B1 | 1/2003 | Ario et al. |
| 6,513,897 B2 | 2/2003 | Tokie |
| 6,528,555 B1 * | 3/2003 | Nikutowski et al. ......... 523/116 |
| 6,566,413 B1 | 5/2003 | Weinmann et al. |
| 6,572,693 B1 | 6/2003 | Wu et al. |
| 6,605,651 B1 * | 8/2003 | Stangel et al. ............... 523/116 |
| 6,652,970 B1 | 11/2003 | Everaerts et al. |
| 6,669,927 B2 | 12/2003 | Trom et al. |
| 6,670,436 B2 | 12/2003 | Burgath et al. |
| 6,759,177 B2 | 7/2004 | Shimada et al. |
| 6,765,036 B2 | 7/2004 | Dede et al. |
| 6,765,038 B2 | 7/2004 | Mitra |
| 6,825,315 B2 | 11/2004 | Aubert |
| 6,960,079 B2 | 11/2005 | Brennan et al. |
| 7,189,489 B2 | 3/2007 | Kunimoto et al. |
| 2002/0013382 A1 | 1/2002 | Furman et al. |
| 2003/0035899 A1 | 2/2003 | Klettke et al. |
| 2003/0054288 A1 | 3/2003 | Shimada et al. |
| 2003/0099762 A1 | 5/2003 | Zhang et al. |
| 2003/0114553 A1 | 6/2003 | Karim et al. |
| 2003/0118970 A1 | 6/2003 | Rusin et al. |
| 2003/0166740 A1 | 9/2003 | Mitra et al. |
| 2003/0181541 A1 | 9/2003 | Wu et al. |
| 2003/0195273 A1 | 10/2003 | Mitra et al. |
| 2003/0196914 A1 | 10/2003 | Tzou et al. |
| 2003/0198914 A1 | 10/2003 | Brennan et al. |
| 2003/0220424 A1 * | 11/2003 | Schofalvi et al. ............ 524/195 |
| 2003/0225183 A1 | 12/2003 | De Putter et al. |
| 2004/0026023 A1 | 2/2004 | DeMeter |
| 2004/0151691 A1 | 8/2004 | Oxman et al. |
| 2004/0162375 A1 | 8/2004 | Ali et al. |
| 2004/0185013 A1 | 9/2004 | Burgio et al. |
| 2004/0206932 A1 | 10/2004 | Abuelyaman |

| | | | |
|---|---|---|---|
| 2005/0070627 | A1 | 3/2005 | Falsafi et al. |
| 2005/0113477 | A1 | 5/2005 | Oxman et al. |
| 2005/0133384 | A1 | 6/2005 | Cinader et al. |
| 2005/0136370 | A1 | 6/2005 | Brennan et al. |
| 2005/0182148 | A1 | 8/2005 | Gaud et al. |
| 2005/0202343 | A1 | 9/2005 | Fujimaki |
| 2005/0252413 | A1 | 11/2005 | Kangas et al. |
| 2005/0252414 | A1 | 11/2005 | Craig et al. |
| 2005/0252415 | A1 | 11/2005 | Budd et al. |
| 2005/0256223 | A1 | 11/2005 | Kolb et al. |

FOREIGN PATENT DOCUMENTS

| | | | |
|---|---|---|---|
| EP | 0 037 677 | A2 | 10/1981 |
| EP | 0 037 677 | A3 | 10/1981 |
| EP | 0 173 567 | A2 | 3/1986 |
| EP | 0 173 567 | A3 | 3/1986 |
| EP | 0 237 233 | A2 | 9/1987 |
| EP | 0 237 233 | A3 | 9/1987 |
| EP | 0 037 677 | B1 | 11/1988 |
| EP | 0 296 384 | A2 | 12/1988 |
| EP | 0 296 384 | A3 | 12/1988 |
| EP | 0 373 384 | | 6/1990 |
| EP | 0 712 622 | A1 | 5/1996 |
| EP | 0 712 622 | B1 | 9/1999 |
| EP | 1 004 279 | A1 | 5/2000 |
| EP | 1 051 961 | A1 | 11/2000 |
| EP | 1 169 995 | A1 | 1/2002 |
| EP | 1 228 744 | A2 | 8/2002 |
| EP | 1 228 744 | A3 | 8/2002 |
| EP | 1 352 617 | A1 | 10/2003 |
| EP | 1 475 069 | A1 | 11/2004 |
| EP | 1 004 279 | B1 | 7/2005 |
| EP | 1 228 744 | B1 | 8/2005 |
| EP | 1 051 961 | B1 | 2/2006 |
| GB | 1550811 | | 8/1979 |
| JP | 5-85912 | | 4/1993 |
| JP | 5-170619 | | 7/1993 |
| JP | 5-245167 | | 9/1993 |
| JP | 9-2916 | | 1/1997 |
| WO | WO 87/01577 | A1 | 3/1987 |
| WO | WO 94/22972 | A1 | 10/1994 |
| WO | WO 98/01103 | A1 | 1/1998 |
| WO | WO 98/09913 | A1 | 3/1998 |
| WO | WO 00/38619 | A2 | 7/2000 |
| WO | WO 00/38619 | A3 | 7/2000 |
| WO | WO 00/42092 | A1 | 7/2000 |
| WO | WO 00/69393 | A1 | 11/2000 |
| WO | WO 01/07444 | A1 | 2/2001 |
| WO | WO 01/30305 | A1 | 5/2001 |
| WO | WO 01/30306 | A1 | 5/2001 |
| WO | WO 01/30307 | A1 | 5/2001 |
| WO | WO 01/51540 | A2 | 7/2001 |
| WO | WO 01/51540 | A3 | 7/2001 |
| WO | WO 01/92271 | A1 | 12/2001 |
| WO | WO 02/092021 | A1 | 11/2002 |
| WO | WO 03/031492 | A1 | 4/2003 |
| WO | WO 03/063804 | A1 | 8/2003 |
| WO | WO 2004/002361 | | 1/2004 |
| WO | WO 2005/018581 | A2 | 3/2005 |
| WO | WO 2005/018581 | A3 | 3/2005 |
| WO | WO 2006/020760 | A1 | 2/2006 |
| WO | WO 2007/075257 | | 7/2007 |
| WO | WO 2007/075663 | | 7/2007 |
| WO | WO 2007/075705 | | 7/2007 |

OTHER PUBLICATIONS

Azzeh et al., "Laser debonding of ceramic brackets: A comprehensive review," *American Journal of Orthodontics and Dentofacial Orthopedics*, Jan. 2003; 123:79-83.

Buonocore et al., "A Report on a Resin Composition Capable of Bonding to Human Dentin Surfaces," *J. Dent. Res.*, 1956, 35(6):846-851.

Laufer et al., "Numerical Analysis of the Thermochemical Tooth Damage Induced by Laser Radiation," *Journal of Biomechanical Engineering*, Aug. 1985; 107:234-239.

Launay et al., "Thermal Effects of Laser on Dental Tissues," *Lasers in Surgery and Medicine*, 7:473-477 (1987).

Mathis et al., "Properties of a New Glass Ionomer/Composite Resin Hybrid Restorative," Abstract No. 51, *J. Dent. Res.*, 66:113 (1987).

Matsuoka, Ed., *Infrared Absorbing Dyes*, Plenum Press, New York (1990).

Rudin, *The Elements of Polymer Science and Engineering*, $2^{nd}$ Edition, Chapter 11, Title page, Publication page, and pp. 377-443 (1999).

Taylor et al., "Positive, Chemically Amplified Aromatic Methacrylate Resist Employing the Tetrahydropyranyl Protecting Group," *Chem. Mater.*, 1991; 3(6):1031-1040.

Uysal et al., *Angle Orthodontist*, 75:220-225 (2005).

Zach et al., "Pulp response to externally applied heat," *Endodontics*, Bender, Ed., pp. 515-530 (1965).

Brandrup et al., Eds., *Polymer Handbook*, $49^{th}$ Edition, (1999), pp. VI/71-VI/93 and VI/193-VI/219.

Crivello et al., *Photoinitiators for Free Radical, Cationic & Anionic Photopolymerization*, vol. 3, $2^{nd}$ Edition, G. Bradley, Editor, Title page, publication page, Table of contents, and Chapter III (pp. 329-478) (1998).

Demus et al., Eds., *Liquid Crystals Handbook*, vols. 1-3 (1998) Thies Thiemann and Volkmar Vill, "General Synthetic Strategies", Chapter 4, vol. 1, pp. 87-113.

Demus et al., Eds., *Liquid Crystals Handbook*, vols. 1-3 (1998) Dietrich Demus, "Chemical Structure and Mesogenic Properties", Chapter 6, vol. 1, pp. 133-187.

Demus et al., Eds., *Liquid Crystals Handbook*, vols. 1-3 (1998) Andrew N. Cammidge and Richard J. Bushby, "Synthesis and Structural Features", Chapter 7, vol. 2B, pp. 693-748.

Demus et al., Eds., *Liquid Crystals Handbook*, vols. 1-3 (1998) Andreas Greiner and Hans-Werner Schmidt, "Synthesis, Structure and Properties", Chapter 1, vol. 3, pp. 3-25.

Greene et al., *Protective Groups in Organic Synthesis*, Wiley-Intersciences, Second Edition (1991), pp. 1-9, 25, 104-111 and 118-126.

Lee and Neville, *Handbook of Epoxy Resins*, McGraw-Hill Book Co., New York (1967), pp. 4-14-4-31.

Smith et al., *March's Advanced Organic Chemistry: Reactions, Mechanisms, and Structure* $5^{th}$ Edition, Wiley (2001) Chapter 10—Aliphatic Nucleophilic Substitution; Section 10-6 Hydrolysis of Acetals, Enol Ethers, and Similar Compounds, pp. 465-468.

Craig and Ward, Eds., *Restorative Dental Materials*, Tenth Edition, Mosby-Year Book, Inc., St. Louis, MO, Chapter 11, © 2002 (Impression Materials).

Yang et al.; Photodegradation of Cyanine and Merocyanine Dyes, Dyes and Pigments 49 (2001) 93-101.

Imaging by Photodecoupling of Crosslinks in Polymer Gels (M-Y Li), Journal of Imaging Science (Nov. 1990), vol. 34, No. 6, Springfield, VA, US.

* cited by examiner

DENTAL COMPOSITIONS INCLUDING RADIATION-TO-HEAT CONVERTERS, AND THE USE THEREOF

BACKGROUND

Orthodontic treatment involves movement of malpositioned teeth to orthodontically correct positions. Tiny orthodontic appliances known as brackets are connected to exterior surfaces of the patient's teeth, and an archwire is placed in a slot of each bracket. The archwire forms a track to guide movement of the teeth to desired positions for correct occlusion. End sections of the archwire are often received in appliances known as buccal tubes that are fixed to the patient's molar teeth. In recent years it has become common practice to use adhesives to bond orthodontic appliances to the surface of the tooth, using either direct or indirect methods. A variety of adhesives are available to the practitioner for bonding brackets to tooth surfaces, and many offer excellent bond strengths. High bond strengths are desirable for maintaining adhesion of the bracket to the tooth surface over the duration of the treatment process, which can typically be two years or more.

However, orthodontic adhesives with high bond strengths can lead to other difficulties. For example, one of the most difficult aspects of the orthodontic treatment process can be the removal of the bracket after completion of treatment. It is well known in the industry that certain adhesives, used in combination with certain rigid brackets, are capable of causing enamel fracture under some debonding conditions. As a result, many commercially available ceramic brackets have been designed for the bond to fail at the interface between the bracket and the adhesive to prevent damage to the tooth surface during the debonding process. However, this approach results in most of the cured adhesive pad being left behind on the tooth surface after the bracket has been removed. Removal of the adhesive pad, which is typically hard and heavily crosslinked, can be time consuming for the clinician and uncomfortable for the patient.

New adhesives and methods are needed that offer satisfactory adhesion of the bracket to the tooth surface throughout the treatment process, and also allow for more convenient removal upon completion of the treatment.

SUMMARY OF THE INVENTION

In one aspect, the present invention provides a method for reducing the bond strength of an orthodontic appliance adhered to a tooth structure with a hardened dental composition (e.g., a hardened orthodontic adhesive, a hardened orthodontic cement, and/or a hardened primer) that includes a radiation-to-heat converter. In one embodiment, the method includes irradiating the hardened dental composition to reduce the bond strength. In some embodiments, irradiating results in heating at least a portion of the hardened dental composition to at least 42° C. Preferably, the hardened dental composition maintains sufficient bond strength prior to irradiation (e.g., throughout the duration of the treatment), but provides reduced bond strength upon irradiation, allowing for convenient removal of the orthodontic appliance from the tooth structure (e.g., less force required to debond the appliance). In some embodiments, the radiation-to-heat converter and/or dental composition including the same, can be placed so as to result in fracture (e.g., adhesive failure) upon debonding at an interface (e.g., an adhesive-tooth interface or an appliance-adhesive interface), or cohesive failure within the hardened dental composition upon debonding. For example, fracture at an adhesive-tooth interface can result in the hardened adhesive being substantially retained on the removed orthodontic appliance, providing for convenient clean-up of the tooth structure.

In another aspect, the present invention provides a hardenable dental composition that includes a radiation-to-heat converter, and/or articles (e.g., orthodontic applicances) having the hardenable and/or hardened dental composition thereon. Optionally, such articles having the hardenable dental composition thereon are provided as precoated articles. Typically, the hardenable dental composition (e.g., an orthodontic primer or an orthodontic adhesive) includes a hardenable component (e.g., an ethylenically unsaturated compound), an initiator, a radiation-to-heat converter, and optionally, a filler. In some embodiments, the hardenable dental composition is a self-etching orthodontic primer or a self-etching orthodontic adhesive that includes an ethylenically unsaturated compound with acid functionality. Optionally, articles having the hardenable and/or hardened dental composition thereon can additionally include one or more layers of different hardenable and/or hardened dental compositions. Methods for making and using such hardenable dental compositions, and/or articles having such hardenable and/or hardened dental compositions thereon, are also provided.

DEFINITIONS

As used herein, "dental composition" refers to a material (e.g., a dental or orthodontic material) capable of adhering (e.g., bonding) to a tooth structure. Dental compositions include, for example, adhesives (e.g., dental and/or orthodontic adhesives), cements (e.g., glass ionomer cements, resin-modified glass ionomer cements, and/or orthodontic cements), primers (e.g., orthodontic primers), restoratives, liners, sealants (e.g., orthodontic sealants), and coatings. Oftentimes a dental composition can be used to bond a dental article to a tooth structure.

As used herein, "dental article" refers to an article that can be adhered (e.g., bonded) to a tooth structure. Dental articles include, for example, crowns, bridges. veneers, inlays, onlays, fillings, orthodontic appliances and devices, and prostheses (e.g., partial or full dentures).

As used herein, "orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e., single or multi-layer adhesives).

As used herein, a "packaged" article refers to an orthodontic appliance or card that is received in a container. Preferably, the container provides protection from environmental conditions including, for example, moisture and light.

As used herein, a "release" substrate refers to a substrate in contact with an article that is removed from the article before or during use of the article.

As used herein, "softening" refers to loss of modulus of a material that can occur as a result of physical and/or chemical changes in the material. The degree of softness or deformability of a material is sometimes referred to as "compliance" of the material, wherein compliance is defined as the inverse of the Young's modulus of the material.

As used herein, "tooth structure" refers to surfaces including, for example, natural and artificial tooth surfaces, bone, tooth models, and the like.

As used herein, a "multi-layer" adhesive refers to an adhesive having two or more distinctly different layers (i.e., layers differing in composition, and preferably having different chemical and/or physical properties).

As used herein, a "layer" refers to a discontinuous (e.g., a patterned layer) or continuous (e.g., non-patterned) material extending across all or a portion of a material different than the layer. The layer may be of uniform or varying thickness.

As used herein, a "patterned layer" refers to a discontinuous material extending across (and optionally attached to) only selected portions of a material different than the patterned layer.

As used herein, a "non-patterned layer" refers to a continuous material extending across (and optionally attached to) an entire portion of a material different than the non-patterned layer.

In general, a layer "on," "extending across," or "attached to" another material different than the layer is intended to be broadly interpreted to optionally include one or more additional layers between the layer and the material different than the layer.

As used herein, "hardenable" is descriptive of a material or composition that can be cured (e.g., polymerized or crosslinked) or solidified, for example, by removing solvent (e.g., by evaporation and/or heating); heating to induce polymerization and/or crosslinking; irradiating to induce polymerization and/or crosslinking; and/or by mixing one or more components to induce polymerization and/or crosslinking. "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

As used herein, "hardened" refers to a material or composition that has been cured (e.g., polymerized or crosslinked) or solidified.

As used herein, "hardener" refers to something that initiates hardening of a resin. A hardener may include, for example, a polymerization initiator system, a photoinitiator system, and/or a redox initiator system.

As used herein, "photobleachable" refers to loss of color upon exposure to actinic radiation.

As used herein, the term "(meth)acrylate" is a shorthand reference to acrylate, methacrylate, or combinations thereof, and "(meth)acrylic" is a shorthand reference to acrylic, methacrylic, or combinations thereof.

As used herein, the chemical term "group" allows for substitution.

As used herein, "a" or "an" means one or more.

BRIEF DESCRIPTION OF THE DRAWINGS

FIG. 9b is a higher magnification view of the nanofibers illustrated in FIG. 9a.

FIG. 10b is a higher magnification view of the nanofibers illustrated in FIG. 10a.

FIG. 11b is a higher magnification view of the nanofibers illustrated in FIG. 11a.

FIG. 12b is a higher magnification view of the nanofibers illustrated in FIG. 12a.

DETAILED DESCRIPTION OF CERTAIN EMBODIMENTS

Figure 1:
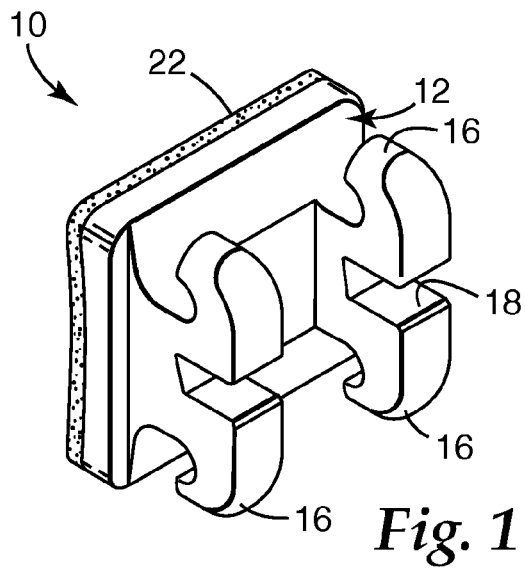
FIG. 1 is perspective view of an orthodontic appliance having a hardenable or hardened dental composition of the present invention on the base thereof.

The present invention provides hardenable dental compositions, and articles including such compositions, that are capable of adhering to a tooth structure upon hardening. Further, the adherence (e.g., bond strength) to the tooth structure of such hardened compositions can be reduced upon irradiating, typically under convenient conditions. The reduced adherence can be useful if and when it is desired to remove the hardened composition from the tooth structure. Such hardenable dental compositions encompass materials (e.g., dental and/or orthodontic materials) capable of adhering (e.g., bonding) to a tooth structure, such as adhesives (e.g., dental and/or orthodontic adhesives), cements (e.g., glass ionomer cements, resin-modified glass ionomer cements), primers, restoratives, liners, sealants, and coatings. Oftentimes a dental composition can be used to bond a dental article (e.g., an orthodontic appliance) to a tooth structure.

In some embodiments, such hardenable dental compositions can, upon hardening, provide sufficient bond strength to adhere an orthodontic appliance to a tooth structure during orthodontic treatment, and are further useful for reducing the bond strength, for example, at the end of the treatment process when it is necessary for the practitioner to remove the appliance from the tooth structure. The compositions, articles, and methods are designed to reduce the bond strength upon irradiating the hardened dental composition under convenient conditions. The resulting reduced bond strength can allow for convenient removal of not only the orthodontic appliance, but also for any hardened dental composition remaining on the tooth structure after removal of the appliance.

Hardenable and hardened dental compositions of the present invention include radiation-to-heat converters, which are described in detail herein. As used herein, a "radiation-to-heat converter" refers to a material or composition that absorbs incident radiation (e.g., visible light, ultraviolet (UV) radiation, infrared (IR) radiation, near infrared (NIR) radiation, and/or radio frequency (RF) radiation) and converts a substantial portion (e.g., at least 50%) of the incident radiation into heat.

A radiation-to-heat converter can be incorporated into a wide variety of dental compositions (e.g., dental and orthodontic materials) including, for example, adhesives, cements (e.g., glass ionomer cements, resin-modified glass ionomer cements), primers, restoratives, liners, sealants, and coatings at levels effective to decrease bond strength of the hardened composition upon heating, while maintaining sufficient adhesion (e.g., of an orthodontic appliance) to the tooth structure during treatment. Treatment can include dental and/or orthodontic treatment processes that last a month, a year, two years, or even longer.

For certain embodiments, such dental compositions can be conveniently applied to the base of an orthodontic appliance by a practitioner. Alternatively, orthodontic appliances can be provided having such dental compositions precoated on the base of the appliance. Typically such precoated appliances are provided as packaged articles with or without a release liner or foam pad liner such as those described, for example, in U.S. Pat. No. 6,183,249 (Brennan et al.). Exemplary containers are well known in the art and are disclosed, for example, in U.S. Pat. Nos. 5,172,809 (Jacobs et al.) and 6,089,861 (Kelly et al.).

Hardenable dental compositions of the present invention typically include an ethylenically unsaturated compound, an initiator, and a radiation-to-heat converter. In some embodiments, the hardenable dental composition also includes a filler. In some embodiments, the hardenable dental composition further includes an ethylenically unsaturated compound with acid functionality, wherein the hardenable dental composition can be, for example, a self-etching orthodontic primer or a self-etching orthodontic adhesive. Optionally, the hardenable dental composition of the present invention can include a thermally responsive additive; a thermally labile component; and/or an acid-generating component and an acid-reactive component as described hereinafter. Preferably, such compositions, upon hardening, can bond an orthodontic appliance to a tooth structure with a bond strength (using the shear peel test method described herein) of at least 7 MPa at room temperature.

Radiation-to-Heat Converter

Hardenable and hardened dental compositions of the present invention include a radiation-to-heat converter, which can allow for heating the hardened dental composition by irradiating the composition. A radiation-to-heat converter is typically a radiation absorber that absorbs incident radiation and converts at least a portion (e.g., at least 50%) of the incident radiation into heat. In some embodiments, the radiation-to-heat converter can absorb light in the infrared, visible, or ultraviolet regions of the electromagnetic spectrum and convert the absorbed radiation into heat. In other embodiments, the radiation-to-heat converter can absorb radio frequency (RF) radiation and convert the absorbed radiation into heat. The radiation absorber(s) are typically highly absorptive of the selected imaging radiation.

A wide variety of radiation-to-heat converters can be used including, for example, organic compounds, inorganic compounds, and metal-organic compounds. Such radiation-to-heat converters can include, for example, dyes (e.g., visible dyes, ultraviolet dyes, infrared dyes, fluorescent dyes, and radiation-polarizing dyes), pigments, metals, metal compounds, metal films, and other suitable absorbing materials. Many classes of organic and metal-organic dyes are described in "Infrared Absorbing Dyes", edited by Masaru Matsuoka, Plenum Press (New York, 1990). These classes of dyes include azo dyes, pyrazolone azo dyes, methine and cyanine dyes, porphyrin dyes, phthalocyanine dyes, quinine dyes such as anthraquinones and naphthaquinones, pyrylium and squarylium dyes, aminium and diimonium dyes. See, also, U.S. Pat. No. 6,759,177 (Shimada et al.). Radiation-to-heat converters can be selected as desired by one of skill in the art based on properties including, for example, solubility in and/or compatibility with the specific hardenable dental composition or solvent therefore, as well as the wavelength range of absorption. Typically, dyes and/or pigments are preferred for use as radiation-to-heat converters that absorb light in the infrared, visible, or ultraviolet regions of the electromagnetic spectrum.

For some embodiments, near infrared (NIR) absorbing pigments and/or dyes are preferred by use as radiation-to-heat converters to allow for heating by irradiating with NIR radiation. Such NIR absorbing materials typically absorb at wavelengths greater than 750 nanometers, and sometimes at wavelengths greater than 800, 850, or even 900 nanometers. Such NIR absorbing materials typically absorb at wavelengths less than 2000 nanometers, and sometimes at wavelengths less than 1500, 1200, or even 1000 nanometers.

A wide variety of pigments and/or dyes can be used as NIR absorbing radiation-to-heat converters. Useful pigments include, for example, indium tin oxide (ITO), antimony tin oxide (ATO), other tin oxide pigments, lanthanum hexaboride ($LAB_6$), porphyrin and phthalocyanine pigments, thioindigo pigments, carbon black, azo pigments, quinacridone pigments, nitroso pigments, natural pigments, and azine pigments. Useful dyes include, for example, NIR absorbing cyanine dyes, NIR absorbing azo dyes, NIR absorbing pyrazolone dyes, NIR absorbing phthalocyanine dyes, NIR absorbing anthraquinone and naphthaquinone dyes, nickel or platinum dithiolene complexes, squarilium dyes, carbonium dyes, methine dyes, diimonium dyes, aminium dyes, croconium dyes, quinoneimine dyes, and pyrylium dyes such as those available under the trade designations IR-27 and IR-140 from Sigma-Aldrich (St. Louis, Mo.) or Epolin Inc. (Newark, N.J.).

In some embodiments, the radiation-to-heat converter can be a radio frequency (RF) absorbing magnetic ceramic powder, to allow for heating by irradiating with RF radiation. Exemplary ceramic powders include, for example, NiZn ferrite available under the trade designation FERRITE N23 from National Magnetics Group (Bethlehem, Pa.) with a reported average particle size of 1.0 micrometer and a Curie Temperature $T_c$) of 95° C.; and Mg—Mn—Zn mixed ferrite available under the trade designation FERRITE R from National Magnetics Group (Bethlehem, Pa.) with a reported average particle size of 1.0 micrometer and a Curie Temperature $T_c$) of 90° C. Such ceramic powders are capable of absorbing radio frequency (RF) radiation and thereby increasing in temperature. At the reported Curie Temperatures, the ferrites will no longer absorb RF radiation and continue to increase in temperature. Typical RF radiation useful in this invention has an intensity range of 10 $\mu W/cm^2$ to 100 $\mu W/cm^2$ and a frequency of 10 KHz to 10 KHz.

Useful radiation-to-heat converters can be in the form of particles, fibers, powders, disks, plates, flakes, tubes, films, or combinations thereof. The radiation-to-heat converter can be dissolved, dispersed, or suspended in a hardenable dental composition that subsequently is hardened. In some embodiments, the radiation-to-heat converter can be distributed uniformly throughout the hardenable dental composition. In other embodiments, especially for embodiments in which the hardenable dental composition is precoated on the base of an orthodontic appliance, the radiation-to-heat converter can be concentrated in a portion of the hardenable dental composition. For example, the radiation-to-heat converter can be concentrated near one surface or on one surface (e.g., the outer surface that will contact the tooth structure) to influence the fracture to occur near the tooth structure upon debonding. Radiation-to-heat converters concentrated near one surface is meant to include radiation-to-heat converters adhered to a surface of the hardenable or hardened dental composition. When particulate radiation-to-heat converters are dispersed in the hardenable dental composition, the average particle size can be, at least in some instances, 10 micrometers or less, and may even be 1 micrometer or less. As used herein for non-spherical particles, "particle size" refers to the smallest dimension of the particle.

Preferred radiation-to-heat converters are those materials having little color together with low toxicity for the oral environment. Typically, useful materials can be easily dispersed in the hardenable dental composition, optionally using dispersing aids to promote dispersion. Alternatively, another material (e.g., a thermally responsive additive) can be coated onto the radiation-to-heat converter, and these hybrid particles can then be mixed into a hardenable dental composition using standard mixing techniques. Alternatively, another material (e.g., a thermally responsive additive) and the radiation-to-heat converter can be mixed together to ensure intimate contact prior to mixing into the hardenable dental composition. In other situations, all or a portion of the dry ingredients (e.g., including other fillers) may be added at the same time to a resin to provide a uniformly mixed composition. Preferred radiation-to-heat converters do not unduly influence polymerization kinetics (e.g., setting time/working time) of the hardenable dental composition, and do not compromise basic properties of either the unhardened dental composition (e.g., original and aged handling properties) or the hardened dental composition (e.g., bond strength).

Hardenable and hardened dental compositions of the present invention preferably include a sufficient amount of radiation-to-heat converter to heat the dental composition, upon irradiation, to a temperature within the range of 42° C. to 200° C., and typically to a temperature no greater than 150° C., and sometimes no greater than 100° C., or even 80° C. Typically and preferably, a hardened dental composition including a radiation-to-heat converter shows lower bond strength at an elevated temperature (e.g., no greater than 200° C., preferably no greater than 150° C., more preferably no greater than 100° C., and most preferably no greater than 80° C.). Specifically, upon irradiation, the hardened dental composition is heated to an elevated temperature (i.e., at least 42° C.), and the bond strength of the hardened dental composition at the elevated temperature decreases. Preferably, the bond strength of the dental composition at the elevated temperature (e.g., 70° C.) is at most 90%, more preferably at most 80%, 50%, 30%, 20%, or even 10% of the bond strength of the hardened dental composition not including the thermally responsive additive at the same elevated temperature (e.g., 70° C.). Further, in certain embodiments it is preferred that bond strengths at the elevated temperature be maintained at a sufficient level (e.g., to avoid having brackets falling off into the patient's mouth before pressure is applied by the practitioner). In such embodiments, it is preferred that the bond strength of the dental composition at the elevated temperature (e.g., upon exposure to hot foods) is at least 5 MPa at the elevated temperature.

Although levels of radiation-to-heat converter will depend on, for example, the specific dental composition being used, typically the hardenable dental composition will include at least 1 part per million, and sometimes at least 25, or even 250 parts per million radiation-to-heat converter, based on the total weight of the dental composition. In some embodiments, the dental composition will include at most 10% by weight, and sometimes at most 5%, or even 3% by weight radiation-to-heat converter, based on the total weight of the dental composition.

Hardenable Component

The hardenable dental compositions of the present invention typically include a hardenable (e.g., polymerizable) component, thereby forming hardenable (e.g., polymerizable) compositions. The hardenable component can include a wide variety of chemistries, such as ethylenically unsaturated compounds (with or without acid functionality), epoxy (oxirane) resins, vinyl ethers, photopolymerization systems, redox cure systems, glass ionomer cements, polyethers, polysiloxanes, and the like. In some embodiments, the compositions can be hardened (e.g., polymerized by conventional photopolymerization and/or chemical polymerization techniques) prior to applying the hardened dental composition. In other embodiments, a dental composition can be hardened (e.g., polymerized by conventional photopolymerization and/or chemical polymerization techniques) after applying the dental composition.

In certain embodiments, the compositions are photopolymerizable, i.e., the compositions contain a photoinitiator (i.e., a photoinitiator system) that upon irradiation with actinic radiation initiates the polymerization (or hardening) of the composition. Such photopolymerizable compositions can be free radically polymerizable or cationically polymerizable. In other embodiments, the compositions are chemically hardenable, i.e., the compositions contain a chemical initiator (i.e., initiator system) that can polymerize, cure, or otherwise harden the composition without dependence on irradiation with actinic radiation. Such chemically hardenable compositions are sometimes referred to as "self-cure" compositions and may include glass ionomer cements (e.g., conventional and resin-modified glass ionomer cements), redox cure systems, and combinations thereof.

Suitable photopolymerizable components that can be used in the dental compositions of the present invention include, for example, epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Also suitable are polymerizable materials that contain both a cationically active functional group and a free radically active functional group in a single compound. Examples include epoxy-functional acrylates, epoxy-functional methacrylates, and combinations thereof.

Ethylenically Unsaturated Compounds

The compositions of the present invention may include one or more hardenable components in the form of ethylenically unsaturated compounds with or without acid functionality, thereby forming hardenable compositions.

Suitable hardenable compositions may include hardenable components (e.g., photopolymerizable compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

The compositions (e.g., photopolymerizable compositions) may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl(meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone(meth)acrylamide; urethane(meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The hardenable component may also contain hydroxyl groups and ethylenically unsaturated groups in a single molecule. Examples of such materials include hydroxyalkyl (meth)acrylates, such as 2-hydroxyethyl(meth)acrylate and 2-hydroxypropyl(meth)acrylate; glycerol mono- or di-(meth) acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis [4-(2-hydroxy-3-ethacryloxypropoxy)phenyl]propane (bis-GMA). Suitable ethylenically unsaturated compounds are also available from a wide variety of commercial sources, such as Sigma-Aldrich, St. Louis. Mixtures of ethylenically unsaturated compounds can be used if desired.

In certain embodiments hardenable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the hardenable components can be used if desired.

Preferably, compositions of the present invention include at least 5% by weight, more preferably at least 10% by weight, and most preferably at least 15% by weight ethylenically unsaturated compounds, based on the total weight of the unfilled composition. Preferably, compositions of the present invention include at most 95% by weight, more preferably at most 90% by weight, and most preferably at most 80% by weight ethylenically unsaturated compounds, based on the total weight of the unfilled composition.

Preferably, compositions of the present invention include ethylenically unsaturated compounds without acid functionality. Preferably, compositions of the present invention include at least 5% by weight (wt-%), more preferably at least 10% by weight, and most preferably at least 15% by weight ethylenically unsaturated compounds without acid functionality, based on the total weight of the unfilled composition. Preferably, compositions of the present invention include at most 95% by weight, more preferably at most 90% by weight, and most preferably at most 80% by weight ethylenically unsaturated compounds without acid functionality, based on the total weight of the unfilled composition.

Ethylenically Unsaturated Compounds with Acid Functionality

The compositions of the present invention may include one or more hardenable components in the form of ethylenically unsaturated compounds with acid functionality, thereby forming hardenable compositions.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl(meth) acrylate (e.g., HEMA) phosphates, bis((meth)acryloxyethyl) phosphate, ((meth)acryloxypropyl)phosphate, bis((meth) acryloxypropyl)phosphate, bis((meth)acryloxy)propyloxy phosphate, (meth)acryloxyhexyl phosphate, bis((meth)acryloxyhexyl)phosphate, (meth)acryloxyoctyl phosphate, bis ((meth)acryloxyoctyl)phosphate, (meth)acryloxydecyl phosphate, bis((meth)acryloxydecyl)phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly (meth)acrylated polysulfonate, poly(meth)acrylated polyboric acid, and the like, may be used as components in the hardenable component system. Also monomers, oligomers, and polymers of unsaturated carbonic acids such as (meth) acrylic acids, aromatic (meth)acrylated acids (e.g., methacrylated trimellitic acids), and anhydrides thereof can be used. Certain preferred compositions of the present invention include an ethylenically unsaturated compound with acid functionality having at least one P—OH moiety.

Certain of these compounds are obtained, for example, as reaction products between isocyanatoalkyl(meth)acrylates and carboxylic acids. Additional compounds of this type having both acid-functional and ethylenically unsaturated components are described in U.S. Pat. Nos. 4,872,936 (Engelbrecht) and 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Pat. Publication No. 2004/0206932 (Abuelyaman et al.); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. Nos. 4,259,075 (Yamauchi et al.), 4,499,251 (Omura et al.), 4,537,940 (Omura et al.), 4,539,382 (Omura et al.), 5,530,038 (Yamamoto et al.), 6,458,868 (Okada et al.), and European Pat. Application Publication Nos. EP 712,622 (Tokuyama Corp.) and EP 1,051,961 (Kuraray Co., Ltd.).

Compositions of the present invention can also include compositions that include combinations of ethylenically unsaturated compounds with acid functionality. Preferably the compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C1-C4 hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C5-C12 hydrocarbon group; an ethylenically unsaturated compound without acid functionality; an initiator system; and a filler. Such compositions are described, for example, in U.S. Provisional Application Ser. No. 60/600,658 (Luchterhandt et al.), filed on Aug. 11, 2004.

Preferably, the compositions of the present invention include at least 1% by weight, more preferably at least 3% by weight, and most preferably at least 5% by weight ethylenically unsaturated compounds with acid functionality, based on the total weight of the unfilled composition. Preferably, compositions of the present invention include at most 80% by weight, more preferably at most 70% by weight, and most preferably at most 60% by weight ethylenically unsaturated compounds with acid functionality, based on the total weight of the unfilled composition.

Epoxy (Oxirane) or Vinyl Ether Compounds

The hardenable compositions of the present invention may include one or more hardenable components in the form of epoxy (oxirane) compounds (which contain cationically active epoxy groups) or vinyl ether compounds (which contain cationically active vinyl ether groups), thereby forming hardenable compositions.

The epoxy or vinyl ether monomers can be used alone as the hardenable component in a dental composition or in combination with other monomer classes, e.g., ethylenically unsaturated compounds as described herein, and can include as part of their chemical structures aromatic groups, aliphatic groups, cycloaliphatic groups, and combinations thereof.

Examples of epoxy (oxirane) compounds include organic compounds having an oxirane ring that is polymerizable by ring opening. These materials include monomeric epoxy compounds and epoxides of the polymeric type and can be aliphatic, cycloaliphatic, aromatic or heterocyclic. These compounds generally have, on the average, at least 1 polymerizable epoxy group per molecule, in some embodiments at least 1.5, and in other embodiments at least 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, carbosilane groups, nitro groups, phosphate groups, and the like. The molecular weight of the epoxy-containing materials may vary from 58 to 100,000 or more.

Suitable epoxy-containing materials useful as the resin system reactive components in the present invention are listed in U.S. Pat. No. 6,187,836 (Oxman et al.) and U.S. Pat. No. 6,084,004 (Weinmann et al.).

Other suitable epoxy resins useful as the resin system reactive components include those which contain cyclohexene oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexyl-methyl)adipate. For a more detailed list of useful epoxides of this nature, reference is made to U.S. Pat. Nos. 6,245,828 (Weinmann et al.) and 5,037,861 (Crivello et al.); and U.S. Pat. Publication No. 2003/035899 (Klettke et al.).

Other epoxy resins that may be useful in the compositions of this invention include glycidyl ether monomers. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)propane). Further examples of epoxides of this type are described in U.S. Pat. No. 3,018,262 (Schroeder), and in "Handbook of Epoxy Resins" by Lee and Neville, McGraw-Hill Book Co., New York (1967).

Other suitable epoxides useful as the resin system reactive components are those that contain silicon, useful examples of which are described in International Pat. Publication No. WO 01/51540 (Klettke et al.).

Additional suitable epoxides useful as the resin system reactive components include octadecylene oxide, epichlorohydrin, styrene oxide, vinyl cyclohexene oxide, glycidol, glycidylmethacrylate, diglycidyl ether of Bisphenol A and other commercially available epoxides, as provided in U.S. Pat. No. 7,262,228 (Oxman et al.).

Blends of various epoxy-containing materials are also contemplated. Examples of such blends include two or more weight average molecular weight distributions of epoxy-containing compounds, such as low molecular weight (below 200), intermediate molecular weight (200 to 10,000) and higher molecular weight (above 10,000). Alternatively or additionally, the epoxy resin may contain a blend of epoxy-containing materials having different chemical natures, such as aliphatic and aromatic, or functionalities, such as polar and non-polar.

Other types of useful hardenable components having cationically active functional groups include vinyl ethers, oxetanes, spiro-orthocarbonates, spiro-orthoesters, and the like.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the CYCLOMER series, such as CYCLOMER M-100, M-101, or A-200 available from Daicel Chemical, Japan, and EBECRYL-3605 available from Radcure Specialties, UCB Chemicals, Atlanta, Ga.

The cationically curable components may further include a hydroxyl-containing organic material. Suitable hydroxyl-containing materials may be any organic material having hydroxyl functionality of at least 1, and preferably at least 2. Preferably, the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights (i.e., from 32 to 200), intermediate molecular weights (i.e., from 200 to 10,000, or high molecular weights (i.e., above 10,000). As used herein, all molecular weights are weight average molecular weights.

The hydroxyl-containing materials may be non-aromatic in nature or may contain aromatic functionality. The hydroxyl-containing material may optionally contain heteroatoms in the backbone of the molecule, such as nitrogen, oxygen, sulfur, and the like. The hydroxyl-containing material may, for example, be selected from naturally occurring or synthetically prepared cellulosic materials. The hydroxyl-containing material should be substantially free of groups which may be thermally or photolytically unstable; that is, the material should not decompose or liberate volatile components at temperatures below 100° C. or in the presence of actinic light which may be encountered during the desired photopolymerization conditions for the polymerizable compositions.

Suitable hydroxyl-containing materials useful in the present invention are listed in U.S. Pat. No. 6,187,836 (Oxman et al.).

The hardenable component(s) may also contain hydroxyl groups and cationically active functional groups in a single molecule. An example is a single molecule that includes both hydroxyl groups and epoxy groups.

Glass Ionomers

The hardenable compositions of the present invention may include glass ionomer cements such as conventional glass ionomer cements that typically employ as their main ingredients a homopolymer or copolymer of an ethylenically unsaturated carboxylic acid (e.g., poly acrylic acid, copoly (acrylic, itaconic acid), and the like), a fluoroaluminosilicate ("FAS") glass, water, and a chelating agent such as tartaric acid. Conventional glass ionomers (i.e., glass ionomer cements) typically are supplied in powder/liquid formulations that are mixed just before use. The mixture will undergo self-hardening in the dark due to an ionic reaction between the acidic repeating units of the polycarboxylic acid and cations leached from the glass.

The glass ionomer cements may also include resin-modified glass ionomer ("RMGI") cements. Like a conventional glass ionomer, an RMGI cement employs an FAS glass. However, the organic portion of an RMGI is different. In one type of RMGI, the polycarboxylic acid is modified to replace or end-cap some of the acidic repeating units with pendent curable groups and a photoinitiator is added to provide a second cure mechanism, e.g., as described in U.S. Pat. No. 5,130,347 (Mitra). Acrylate or methacrylate groups are usually employed as the pendant curable group. In another type of RMGI, the cement includes a polycarboxylic acid, an acrylate or methacrylate-functional monomer and a photoinitiator, e.g., as in Mathis et al., "Properties of a New Glass Ionomer/Composite Resin Hybrid Restorative", Abstract No. 51, J. Dent Res., 66:113 (1987) and as in U.S. Pat. Nos. 5,063,257 (Akahane et al.), 5,520,725 (Kato et al.), 5,859,089 (Qian), 5,925,715 (Mitra) and 5,962,550 (Akahane et al.). In another type of RMGI, the cement may include a polycarboxylic acid, an acrylate or methacrylate-functional monomer, and a redox or other chemical cure system, e.g., as described in U.S. Pat. Nos. 5,154,762 (Mitra et al.), 5,520,725 (Kato et al.), and 5,871,360 (Kato). In another type of RMGI, the cement may include various monomer-containing or resin-containing components as described in U.S. Pat. Nos. 4,872,936 (Engelbrecht), 5,227,413 (Mitra), 5,367,002 (Huang et al.), and 5,965,632 (Orlowski). RMGI cements are preferably formulated as powder/liquid or paste/paste systems, and contain water as mixed and applied. The compositions are able to harden in the dark due to the ionic reaction between the acidic repeating units of the polycarboxylic acid and cations leached from the glass, and commercial RMGI products typically also cure on exposure of the cement to light from a dental curing lamp. RMGI cements that contain a redox cure system and that can be cured in the dark without the use of actinic radiation are described in U.S. Pat. No. 6,765,038 (Mitra).

Polyethers or Polysiloxanes (i.e. Silicones)

Dental impression materials are typically based on polyether or polysiloxane (i.e. silicone) chemistry. Polyether materials typically consist of a two-part system that includes a base component (e.g., a polyether with ethylene imine rings as terminal groups) and a catalyst (or accelerator) component (e.g., an aryl sulfonate as a cross-linking agent). Polysiloxane materials also typically consist of a two-part system that includes a base component (e.g., a polysiloxane, such as a dimethylpolysiloxane, of low to moderately low molecular weight) and a catalyst (or accelerator) component (e.g., a low to moderately low molecular weight polymer with vinyl terminal groups and chloroplatinic acid catalyst in the case of addition silicones; or a liquid that consists of stannous octanoate suspension and an alkyl silicate in the case of condensation silicones). Both systems also typically contain a filler, a plasticizer, a thickening agent, a coloring agent, or mixtures thereof. Exemplary polyether impression materials include those described in, for example, U.S. Pat. No. 6,127,449 (Bissinger et al.); U.S. Pat. No. 6,395,801 (Bissinger et al.); and U.S. Pat. No. 5,569,691 (Guggenberger et al.). Exemplary polysiloxane impression materials and related polysiloxane chemistry are described in, for example, U.S. Pat. Nos. 6,121,362 (Wanek et al.) and 6,566,413 Weinmann et al.), and EP Pat. Publication No. 1 475 069 A (Bissinger et al.).

Examples of commercial polyether and polysiloxane impression materials include, but are not limited to, IMPREGUM Polyether Materials, PERMADYNE Polyether Materials, EXPRESS Vinyl Polysiloxane Materials, DIMENSION Vinyl Polysiloxane Materials, and IMPRINT Vinyl Polysiloxane Materials; all available from 3M ESPE (St. Paul, Minn.). Other exemplary polyether, polysiloxane (silicones), and polysulfide impression materials are discussed in the following reference: Restorative Dental Materials, Tenth Edition, edited by Robert G. Craig and Marcus L. Ward, Mosby-Year Book, Inc., St. Louis, Mo., Chapter 11 (Impression Materials).

Photoinitiator Systems

In certain embodiments, the compositions of the present invention are photopolymerizable, i.e., the compositions contain a photopolymerizable component and a photoinitiator (i.e., a photoinitiator system) that upon irradiation with actinic radiation initiates the polymerization (or hardening) of the composition. Such photopolymerizable compositions can be free radically polymerizable or cationically polymerizable.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. Nos. 4,298,738 (Lechtken et al.), 4,324,744 (Lechtken et al.), 4,385,109 (Lechtken et al.), 4,710,523 (Lechtken et al.), and 4,737,593 (Ellrich et al.), 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis (2,6-dimethoxybenzoyl)-(2,4,4-trimethylpentyl)phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

Suitable photoinitiators for polymerizing cationically photopolymerizable compositions include binary and tertiary systems. Typical tertiary photoinitiators include an iodonium salt, a photosensitizer, and an electron donor compound as described in EP 0 897 710 (Weinmann et al.); in U.S. Pat. Nos. 5,856,373 (Kaisaki et al.), 6,084,004 (Weinmann et al.), 6,187,833 (Oxman et al.), and 6,187,836 (Oxman et al.); and in U.S. Pat. No. 6,765,036 (Dede et al.). The compositions of the invention can include one or more anthracene-based compounds as electron donors. In some embodiments, the compositions comprise multiple substituted anthracene compounds or a combination of a substituted anthracene compound with unsubstituted anthracene. The combination of these mixed-anthracene electron donors as part of a photoinitiator system provides significantly enhanced cure depth and cure speed and temperature insensitivity when compared to comparable single-donor photoinitiator systems in the same matrix. Such compositions with anthracene-based electron donors are described in U.S. Pat. No. 7,262,228 (Oxman et al.).

Suitable iodonium salts include tolylcumyliodonium tetrakis(pentafluorophenyl)borate, tolylcumyliodonium tetrakis(3,5-bis(trifluoromethyl)-phenyl)borate, and the diaryl iodonium salts, e.g., diphenyliodonium chloride, diphenyliodonium hexafluorophosphate, diphenyliodonium hexafluoroantimonate, and diphenyliodonium tetrafluoroboarate. Suitable photosensitizers are monoketones and diketones that absorb some light within a range of 450 nm to 520 nm (preferably, 450 nm to 500 nm). More suitable compounds are alpha diketones that have some light absorption within a range of 450 nm to 520 nm (even more preferably, 450 nm to 500 nm). Preferred compounds are camphorquinone, benzil, furil, 3,3,6,6-tetramethylcyclohexanedione, phenanthraquinone and other cyclic alpha diketones. Most preferred is camphorquinone. Suitable electron donor compounds include substituted amines, e.g., ethyl 4-(dimethylamino) benzoate and 2-butoxyethyl 4-(dimethylamino)benzoate; and polycondensed aromatic compounds (e.g. anthracene).

The initiator system is present in an amount sufficient to provide the desired rate of hardening (e.g., polymerizing and/ or crosslinking). For a photoinitiator, this amount will be dependent in part on the light source, the thickness of the layer to be exposed to radiant energy, and the extinction coefficient of the photoinitiator. Preferably, the initiator system is present in a total amount of at least 0.01 wt-%, more preferably, at least 0.03 wt-%, and most preferably, at least 0.05 wt-%, based on the weight of the composition. Preferably, the initiator system is present in a total amount of no more than 10 wt-%, more preferably, no more than 5 wt-%, and most preferably, no more than 2.5 wt-%, based on the weight of the composition.

Redox Initiator Systems

In certain embodiments, the compositions of the present invention are chemically hardenable, i.e., the compositions contain a chemically hardenable component and a chemical initiator (i.e., initiator system) that can polymerize, cure, or otherwise harden the composition without dependence on irradiation with actinic radiation. Such chemically hardenable compositions are sometimes referred to as "self-cure" compositions and may include glass ionomer cements, resin-modified glass ionomer cements, redox cure systems, and combinations thereof.

The chemically hardenable compositions may include redox cure systems that include a hardenable component (e.g., an ethylenically unsaturated polymerizable component) and redox agents that include an oxidizing agent and a reducing agent. Suitable hardenable components, redox agents, optional acid-functional components, and optional fillers that are useful in the present invention are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the hardenable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the hardenable composition except for the optional filler, and observing whether or not a hardened mass is obtained.

Preferably, the reducing agent is present in an amount of at least 0.01% by weight, and more preferably at least 0.1% by weight, based on the total weight (including water) of the components of the hardenable composition. Preferably, the reducing agent is present in an amount of no greater than 10% by weight, and more preferably no greater than 5% by weight, based on the total weight (including water) of the components of the hardenable composition.

Preferably, the oxidizing agent is present in an amount of at least 0.01% by weight, and more preferably at least 0.10% by weight, based on the total weight (including water) of the components of the hardenable composition. Preferably, the oxidizing agent is present in an amount of no greater than 10% by weight, and more preferably no greater than 5% by weight, based on the total weight (including water) of the components of the hardenable composition.

The reducing or oxidizing agents can be microencapsulated as described in U.S. Pat. No. 5,154,762 (Mitra et al.). This will generally enhance shelf stability of the hardenable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a hardenable composition such as described U.S. Pat. No. 5,154,762 (Mitra et al.).

Fillers

The compositions of the present invention can optionally contain fillers. Fillers may be selected from one or more of a wide variety of materials suitable for incorporation in compositions used for dental applications, such as fillers currently used in dental restorative compositions, and the like.

The filler is preferably finely divided. The filler can have a unimodial or polymodial (e.g., bimodal) particle size distribution. Preferably, the maximum particle size (the largest dimension of a particle, typically, the diameter) of the filler is less than 20 micrometers, more preferably less than 10 micrometers, and most preferably less than 5 micrometers. Preferably, the average particle size of the filler is less than 0.1 micrometers, and more preferably less than 0.075 micrometer.

The filler can be an inorganic material. It can also be a crosslinked organic material that is insoluble in the resin system (i.e., the hardenable components), and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz (i.e., silica, $SiO_2$); nitrides (e.g., silicon nitride); glasses and fillers derived from, for example, Zr, Sr, Ce, Sb, Sn, Ba, Zn, and Al; feldspar; borosilicate glass; kaolin; talc; zirconia; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz (i.e., silica), submicron silica, zirconia, submicron zirconia, and non-vitreous microparticles of the type described in U.S. Pat. No. 4,503,169 (Randklev). Mixtures of these non-acid-reactive fillers are also contemplated, as well as combination fillers made from organic and inorganic materials.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like. Silane-treated zirconia-silica ($ZrO_2$—$SiO_2$) filler, silane-treated silica filler, silane-treated zirconia filler, and combinations thereof are especially preferred in certain embodiments.

Other suitable fillers are disclosed in U.S. Pat. Nos. 6,387,981 (Zhang et al.) and 6,572,693 (Wu et al.) as well as International Application Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,156,911 (Kangas et al.); U.S. Patent Publication No. US2005/0256223 (Kolb et al.); U.S. Pat. No. 7,090,721 (Craig et al.); and U.S. Pat. No. 7,090,722 (Budd et al.). These applications, in summary, describe the following nanofiller containing compositions.

U.S. Pat. No. 7,156,911 (Kangas et al.) describes stable ionomer compositions (e.g., glass ionomer) containing nanofillers that provide the compositions with improved properties over previous ionomer compositions. In one embodiment, the composition is a hardenable dental composition comprising a polyacid (e.g., a polymer having a plurality of acidic repeating groups); an acid-reactive filler; at least 10 percent by weight nanofiller or a combination of nanofillers each having an average particle size no more than 200 nanometers; water; and optionally a polymerizable component (e.g., an ethylenically unsaturated compound, optionally with acid functionality).

U.S. Patent Publication No. US2005/0256223 (Kolb et al.) describes stable ionomer (e.g., glass ionomer) compositions containing nanozirconia fillers that provide the compositions with improved properties, such as ionomer systems that are optically translucent and radiopaque. The nanozirconia is surface modified with silanes to aid in the incorporation of the nanozirconia into ionomer compositions, which generally contain a polyacid that might otherwise interact with the nanozirconia causing coagulation or aggregation resulting in undesired visual opacity. In one aspect, the composition can be a hardenable dental composition including a polyacid; an acid-reactive filler; a nanozirconia filler having a plurality of silane-containing molecules attached onto the outer surface of the zirconia particles; water; and optionally a polymerizable component (e.g., an ethylenically unsaturated compound, optionally with acid functionality).

U.S. Pat. No. 7,090,721 (Craig et al.) describes stable ionomer compositions (e.g., glass ionomers) containing nanofillers that provide the compositions with enhanced optical translucency. In one embodiment, the composition is a hardenable dental composition including a polyacid (e.g., a polymer having a plurality of acidic repeating groups); an acid-reactive filler; a nanofiller; an optional polymerizable component (e.g., an ethylenically unsaturated compound, optionally with acid functionality); and water. The refractive index of the combined mixture (measured in the hardened state or the unhardened state) of the polyacid, nanofiller, water and optional polymerizable component is generally within 4 percent of the refractive index of the acid-reactive filler, typically within 3 percent thereof, more typically within 1 percent thereof, and even more typically within 0.5 percent thereof.

U.S. Pat. No. 7,090,722 (Budd et al.) describes dental compositions that can include an acid-reactive nanofiller (i.e., a nanostructured filler) and a hardenable resin (e.g., a polymerizable ethylenically unsaturated compound. The acid-reactive nanofiller can include an oxyfluoride material that is acid-reactive, non-fused, and includes a trivalent metal (e.g., alumina), oxygen, fluorine, an alkaline earth metal, and optionally silicon and/or a heavy metal.

For some embodiments of the present invention that include filler (e.g., dental adhesive compositions), the compositions preferably include at least 1% by weight, more preferably at least 2% by weight, and most preferably at least 5% by weight filler, based on the total weight of the composition. For such embodiments, compositions of the present invention preferably include at most 40% by weight, more preferably at most 20% by weight, and most preferably at most 15% by weight filler, based on the total weight of the composition.

For other embodiments (e.g., where the composition is a dental restorative or an orthodontic adhesive), compositions of the present invention preferably include at least 40% by weight, more preferably at least 45% by weight, and most preferably at least 50% by weight filler, based on the total weight of the composition. For such embodiments, compositions of the present invention preferably include at most 90% by weight, more preferably at most 80% by weight, even more preferably at most 70% by weight filler, and most preferably at most 50% by weight filler, based on the total weight of the composition.

Optional Photobleachable and/or Thermochromic Dyes

In some embodiments, compositions of the present invention preferably have an initial color remarkably different than dental structures. Color is preferably imparted to the composition through the use of a photobleachable or photochromic dye. The composition preferably includes at least 0.001% by weight photobleachable or photochromic dye, and more preferably at least 0.002% by weight photobleachable or photochromic dye, based on the total weight of the composition. The composition preferably includes at most 1% by weight photobleachable or photochromic dye, and more preferably at most 0.1% by weight photobleachable or photochromic dye, based on the total weight of the composition. The amount of photobleachable and/or photochromic dye may vary depending on its extinction coefficient, the ability of the human eye to discern the initial color, and the desired color change. Suitable photobleachable dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. Preferably, at least one photobleachable dye is at least partially soluble in a hardenable resin.

Exemplary classes of photobleachable dyes are disclosed, for example, in U.S. Pat. Nos. 6,331,080 (Cole et al.), 6,444,725 (Trom et al.), and 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change in the inventive compositions is initiated by light. Preferably, the composition's color change is initiated using actinic radiation using, for example, a dental curing light which emits visible or near infrared (IR) light for a sufficient amount of time. The mechanism that initiates the color change in the compositions of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from an initial color to a final color is preferably quantified by a color test. Using a color test, a value of $\Delta E^*$ is determined, which indicates the total color change in a 3-dimensional color space. The human eye can detect a color change of approximately 3 $\Delta E^*$ units in normal lighting conditions. The dental compositions of the present invention are preferably capable of having a color change, $\Delta E^*$, of at least 20; more preferably, $\Delta E^*$ is at least 30; most preferably $\Delta E^*$ is at least 40.

Optional Acid-Generating Component and Acid-Reactive Component

Optionally, the hardenable dental composition of the present invention can include an acid-generating component and an acid-reactive component as described, for example, in U.S. Patent Publication No. US2007/0142497 (Kalgutkar et al.).

Acid-generating components typically include an acid-generating compound, and optionally a sensitizer. Preferably, the acid-generating component generates an acid upon irradiation (i.e., a photo-acid). Typically, the acid can react with greater than a stoichiometric amount of acid-reactive groups. Preferably, dental compositions of the present invention do not include groups that would act to deplete the generated acid in amounts sufficient to interfere with the desired reaction of the generated acid with the acid-reactive component.

Exemplary acid-generating components include iodonium salts (e.g., diaryliodonium salts), sulfonium salts (e.g., triarylsulfonium salts and dialkylphenacylsulfonium salts), selenonium salts (e.g., triarylselenonium salts), sulfoxonium salts (e.g., triarylsulfoxonium salts, aryloxydiarylsulfoxonium salts, and dialkylphenacylsulfoxonium salts), diazonium salts (e.g., aryldiazonium salts), organometallic complex cations (e.g., ferrocenium salts), halo-S-triazenes, trihaloketones, α-sulfonyloxy ketones, silyl benzyl ethers, and combinations thereof. When the acid-generating component is a salt of a cationic species (e.g., an "onium" salt), typical counterions for the salt include, for example, tetrafluoroborate, hexafluorophosphate, hexafluoroarsenate, hexafluoroantimonate, and combinations thereof. Exemplary acid-generating components include those disclosed, for example, in Crivello et al., "Photoinitiators for Free Radical, Cationic and Anionic Photopolymerization," G. Bradley, Editor, Volume 3, Chapter 6 (1998), and U.S. Pat. Nos. 6,187,833 (Oxman et al.), 6,395,124 (Oxman et al.), 6,765,036 (Dede et al.), 3,775,113 (Bonham et al.), 3,779,778 (Smith et al.), 3,954,475 (Bonham et al.), 4,329,384 (Vesley et al.), 4,330,570 (Giuliani et al.), 5,089,374 (Saeva), and 5,141,969 (Saeve et al.).

Preferably the acid-generating component includes a sulfonium salt. Exemplary sulfonium salts include, for example, triaryl sulfonium hexafluoroantimonate ($Ar_3S^+SbF_6^-$, available under the trade designation CYRACURE CPI-6976 from Advanced Research Corporation, Catoosa, Okla.); triaryl sulfonium hexafluorophosphate ($Ar_3S^+PF_6^-$, 50% solution in propylene carbonate, available under the trade designation CYRACURE CPI-6992, from Aceto Corp., Lake Success, N.Y.); and triaryl sulfonium N-(trifluoromethanesulfonyl)trifluoromethane-sulfonamido anion ($Ar_3S_+N(SO_2CF_3)_2)^-$, which can be prepared as generally described in U.S. Pat. No. 5,554,664 (Lamanna et al.).

Exemplary sensitizers include anthracene derivatives (e.g., 2-methylanthracene (2-MA, Sigma-Aldrich) and 2-ethyl-9,10-dimethoxyanthracene (EDMOA, Sigma-Aldrich)), perylene, phenothiazene, and other polycyclic aromatic compounds as described, for example, in U.S. Pat. No. 6,765,036 (Dede et al.) and U.S. Pat. Publication No. 2005/0113477 (Oxman et al.), and combinations thereof. One of skill in the art could select, without undue experimentation, an appropriate sensitizer for sensitizing a specific acid-generating component (e.g., a sulfonium salt) based on the principles described, for example, in Crivello et al., "Photoinitiators for Free Radical, Cationic and Anionic Photopolymerization," G. Bradley, Editor, Volume 3, Chapter 6 (1998). Preferably, a sensitizer can be selected that absorbs at a different wavelength than the photoinitiator; has a singlet or triplet state that is higher in energy than the corresponding singlet or triplet state in the acid-generating component; and/or has an oxidation potential such that reduction of the acid-generating component is energetically favorable. For example, 2-methylanthracene is an appropriate sensitizer for sensitizing triaryl sulfonium hexafluoroantimonate.

As used herein, an "acid-reactive component" refers to a component (typically a compound) that includes one or more acid-reactive groups. As used herein, an "acid-reactive group" refers to a group that undergoes, after reaction with an acid, substantial breaking (e.g., observable by spectroscopic techniques) of chemical bonds within the group to form two or more separate groups, often upon heating to an elevated temperature (i.e., at least 42° C.). Preferably, the elevated temperature is no greater than 200° C., more preferably no greater than 150° C., and even more preferably no greater than 100° C., and most preferably no greater than 80° C. Suitable methods for determining whether substantial breaking of chemical bonds occurs after reaction of a component with an acid would be apparent to one of skill in the art. Suitable methods include, for example, spectroscopic methods such as nuclear magnetic resonance (NMR) spectroscopy (including $^1$H, $^{13}$C, and/or other appropriate nuclei); and ultraviolet (UV), visible, and infrared (IR) spectroscopy, including near IR (NIR) spectroscopy. For example, $^1$H and/or $^{13}$C NMR spectra can be conveniently run in an NMR tube by dissolving the component in a non-acidic solvent (e.g., CDCl$_3$), adding an acid (e.g., CF$_3$CO$_2$D), and observing the disappearance of peaks arising from the component or the appearance of peaks arising from a reaction product at the desired temperature.

Acid-reactive components suitable for use in hardenable dental compositions of the present invention are preferably hardenable components that include one or more acid-reactive groups. Typically, each acid-reactive group is a multivalent group linking a plurality (i.e., two or more) of hardenable groups. In certain embodiments, the hardenable acid-reactive component is an ethylenically unsaturated compound. For example, in such embodiments, the acid-reactive group can be a divalent group linking two ethylenically unsaturated groups.

Acid reactive groups are well known in the art. Such groups include, for example, functionalities typically used in protection methodologies in organic synthesis, where the protecting group can be designed for removal under acidic conditions. See, for example, Greene et al. *Protective Groups in Organic Synthesis*, Wiley-Interscience (1999); Taylor et al., *Chem. Mater.*, 3:1031-1040 (1991); and U.S. Pat. No. 6,652,970 (Everaerts et al.).

Optional Thermally Labile Comonents

Optionally, the hardenable dental composition of the present invention can include a thermally labile component as described, for example, in U.S. Patent Publication No. US2007/0142494 (Kalgutkar et al.).

As used herein, a "thermally labile component" refers to a component (typically a compound) that includes one or more thermally labile groups. As used herein, a "thermally labile group" refers to a group that undergoes substantial breaking (e.g., observable by spectroscopic techniques) of chemical bonds within the group to form two or more separate groups upon heating to an elevated temperature (i.e., at least 42° C.). Preferably, the elevated temperature is no greater than 200° C., more preferably no greater than 150° C., and even more preferably no greater than 100° C., and most preferably no greater than 80° C. Suitable methods for determining whether substantial breaking of chemical bonds occurs upon heating a component to an elevated temperature would be apparent to one of skill in the art. Suitable methods include, for example, spectroscopic methods such as nuclear magnetic resonance (NMR) spectroscopy (including $^1$H, $^{13}$C, and/or other appropriate nuclei); and ultraviolet (UV), visible, and infrared (IR) spectroscopy, including near IR (NIR) spectroscopy. For example, $^1$H and/or $^{13}$C NMR spectra can be conveniently run in an NMR tube by dissolving the component in a solvent (e.g., CDCl$_3$), heating to an elevated temperature, and observing the disappearance of peaks arising from the component or the appearance of peaks arising from a reaction product at the desired temperature.

In certain embodiments, thermally labile components suitable for use in hardenable dental compositions of the present invention are preferably hardenable components that include one or more thermally labile groups. Typically, each thermally labile group is a multivalent group linking a plurality (i.e., two or more) of hardenable groups. In certain embodiments, the hardenable thermally labile component is an ethylenically unsaturated compound. For example, in such embodiments, the thermally labile group can be a divalent group linking two ethylenically unsaturated groups.

Thermally labile groups are well known in the art. Such groups include, for example, oxime esters as disclosed, for example, in U.S. Pat. No. 6,652,970 (Everaerts et al.), and groups including cycloaddition adducts as disclosed, for example, in U.S. Pat. Nos. 6,825,315 (Aubert), 6,147,141 (Iyer et al.), and PCT International Patent Application Publication No. WO 98/09913 (Rotello).

Optional Thermally Responsive Additives

Optionally, the hardenable dental composition of the present invention can include a thermally responsive additive as described, for example, in U.S. Patent Publication No. US2007/0142498 (Brennan et al.).

As used herein, a "thermally responsive additive" is meant to include an additive that softens upon heating to a temperature (e.g., no greater than 200° C., preferably no greater than 150° C., more preferably no greater than 100° C., and most preferably no greater than 80° C.) that is below the decomposition temperature of the additive. Specifically, upon heating to an elevated temperature (i.e., at least 42° C.), the storage modulus of the additive at the elevated temperature decreases compared to the storage modulus of the additive at room temperature (e.g., 25° C.). Preferably, the storage modulus of the additive at the elevated temperature is at most 80%, more preferably at most 60%, 40%, 20%, 10%, 5%, 2%, 1%, 0.1%, or even 0.01% of the storage modulus of the additive at room temperature. Methods of measuring storage modulus of materials at specified temperatures are well known in the art and include those described, for example, in Rudin, "The Elements of Polymer Science and Engineering," 2$^{nd}$ Ed, Chapter 11, pp. (1999). Such methods include, for example, dynamic mechanical measurements by techniques such as dynamic mechanical analysis (DMA).

Such thermally responsive additives typically have a maximum in the rate of storage modulus decrease occurring typically within the range of 42° C. to 200° C. Such a maximum in the rate of storage modulus decrease can correspond to transitions including, for example, melt transitions (T$_m$), glass transitions (T$_g$), solid to smectic or nematic phase transitions in liquid crystals, isotropic melt transitions in liquid crystals, and the like.

In certain embodiments, softening of a hardened dental composition including a thermally responsive additive, upon heating to a temperature (e.g., no greater than 200° C., preferably no greater than 150° C., more preferably no greater than 100° C., and most preferably no greater than 80° C.) that is below the decomposition temperature of the additive, may optionally, but not necessarily, be observed to a greater extent than for the hardened dental composition not including a thermally responsive additive under similar conditions.

In some embodiments, thermally responsive additives can be polymers. Polymers having a wide variety of morphologies can be used. For example, a thermally responsive additive can be a semicrystalline polymer, an amorphous polymer, or a combination thereof. In some embodiments, thermally responsive additives can be liquid crystals (e.g., non-polymeric liquid crystals or polymeric liquid crystals). In some embodiments, thermally responsive additives can be waxes.

Useful semicrystalline polymers typically have a melt transition temperature (T$_m$) of at least 42° C. Useful semicrystalline polymers typically have a melt transition temperature ($T_m$) of at most 200° C., preferably at most 150° C., more preferably at most 100° C., and most preferably no greater than 80° C.

Useful amorphous polymers typically have a glass transition temperature ($T_g$) of at least 42° C. Useful amorphous polymers typically have a glass transition temperature ($T_g$) of at most 200° C., preferably at most 150° C., more preferably at most 100° C., and most preferably no greater than 80° C.

Examples of polymer classes that can be used for thermally responsive additives include poly((meth)acrylics), poly((meth)acrylamides), poly(alkenes), poly(dienes), poly(styrenes), poly(vinyl alcohol), poly(vinyl ketones), poly(vinyl esters), poly(vinyl ethers), poly(vinyl thioethers), poly(vinyl halides), poly(vinyl nitriles), poly(phenylenes), poly(anhydrides), poly(carbonates), poly(esters), poly(lactones), poly(ether ketones), poly(alkylene oxides), poly(urethanes), poly(siloxanes), poly(sulfides), poly(sulfones), poly(sulfonamides), poly(thioesters), poly(amides), poly(anilines), poly(imides), poly(imines), poly(ureas), poly(phosphazenes), poly(silanes), poly(silazanes), carbohydrates, gelatins, poly(acetals), poly(benzoxazoles), poly(carboranes), poly(oxadiazoles), poly(piperazines), poly(piperidines), poly(pyrazoles), poly(pyridines), poly(pyrrolidines), poly(triazines), and combinations thereof. One of skill in the art could select, without undue experimentation, polymers from the above-recited classes that have desired transition temperatures. See, for example, "Polymer Handbook," 4$^{th}$ Edition edited by J. Brandrup et al. (1999) for a list of melt transition temperatures and glass transition temperatures of selected polymers.

A wide variety of liquid crystals can be used for thermally responsive additives including, for example, those recited in "Liquid Crystals Handbook," volumes 1-3, edited by Demus et al. (1998). Suitable liquid crystals typically have an isotropic transition temperature of at least 42° C. Suitable liquid crystals typically have an isotropic transition temperature of at most 200° C., preferably at most 150° C., more preferably at most 100° C., and most preferably no greater than 80° C. One of skill in the art could select, without undue experimentation, liquid crystals that have desired transition temperatures.

Useful classes of liquid crystals include, for example, biphenyls (e.g., R-Ph-Ph-CN); terphenyls (e.g., R-Ph-Ph-Ph-CN); esters (e.g., R-PhC(O)O-Ph-OR', R-PhC(O)O-Ph-CN, and R-PhC(O)O-Ph-Ph-CN); tolanes (e.g., R-Ph-C≡C-Ph-OR'); Schiff's bases (e.g., R-Ph-N═CH-Ph-OR' and R—O—Ph-CH═N-Ph-CN); azo compounds (R-Ph-N═N-Ph-OR'); azoxy compounds (e.g., R-Ph-N═N$^+$(O$^-$)-Ph-OR'); and stilbenes (e.g., R-Ph-C(Cl)═CH-Ph-OR'), where each R and R' independently represent an alkyl group. R is preferably a higher alkyl group, and typically at least a C7 alkyl group, and sometimes at least a C12 alkyl group. R' is preferably a lower alkyl group, and typically a C1 or C2 alkyl group.

Examples of waxes that can be used for thermally responsive additives include dental waxes such as pattern wax, baseplate wax, sheet wax, impression wax, study wax, polycaprolactone, polyvinylacetate, ethylene-vinyl acetate copolymer, polyethylene glycol, esters of carboxylic acids with long chain alcohols (e.g., behenyl acrylate), esters of long chain carboxylic acids with long chain alcohols (e.g., beeswax, a non-polymeric wax), petroleum waxes, oxidized polyethylene wax (e.g., a wax available under the trade designation CERIDUST 3719 from Clariant Corp., Charlotte, N.C.), micronized, polar, high density polyethylene wax (e.g., a wax available under the trade designation CERIDUST 3731 from Clariant Corp., Charlotte, N.C.), carnauba wax (e.g., a wax available under the trade designation MIWAX from Michelman Incorporated, Cinncinnati, Ohio), and combinations thereof (e.g., blends including two or more of microcystalline waxes, carnauba wax, ceresin, and beeswax). Useful waxes can also be oligomeric or polymeric. Useful waxes can be macrocrystalline or microcrystalline, natural or synthetic, and they may contain functional groups (e.g., carboxyl, alcohol, ester, ketone, and/or amide groups). Suitable waxes melt at or above room temperature (e.g., 25° C.), and typically at or above 40° C., and sometimes at or above 50° C. Suitable waxes typically have low melt temperatures (e.g., no greater than 200° C., preferably no greater than 150° C., more preferably no greater than 100° C., even more preferably no greater than 90° C., and most preferably no greater than 80° C.). Suitable waxes can have a wide variety of physical properties. For example, at room temperature, physical properties of suitable waxes can range from kneadable to hard or brittle; coarse to crystalline; and/or transparent to opaque (with transparent being preferred).

Miscellaneous Optional Additives

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions of the invention can contain additives such as indicators, dyes, pigments, inhibitors, accelerators, viscosity modifiers, wetting agents, buffering agents, stabilizers, and other similar ingredients that will be apparent to those skilled in the art. Viscosity modifiers include the thermally responsive viscosity modifiers (such as PLURONIC F-127 and F-108 available from BASF Wyandotte Corporation, Parsippany, N.J.) and may optionally include a polymerizable moiety on the modifier or a polymerizable component different than the modifier. Such thermally responsive viscosity modifiers are described in U.S. Pat. No. 6,669,927 (Trom et al.) and U.S. Pat. Publication No. 2004/0151691 (Oxman et al.).

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Methods

Hardenable and hardened dental compositions of the present invention (e.g., compositions that in certain embodiments include a radiation-to-heat converter) can be used for a variety of dental and orthodontic applications that utilize a material capable of adhering (e.g., bonding) to a tooth structure. Preferred uses include applications in which it is desired that the hardened dental composition be removed from the tooth structure at some point in time. Uses for such hardenable and hardened dental compositions include, for example, uses as adhesives (e.g., dental and/or orthodontic adhesives), cements (e.g., glass ionomer cements, resin-modified glass ionomer cements, and orthodontic cements), primers (e.g., orthodontic primers), restoratives, liners, sealants (e.g., orthodontic sealants), coatings, and combinations thereof.

One preferred use for such hardenable or hardened dental compositions includes adhering an orthodontic appliance to a tooth structure. Exemplary embodiments for an orthodontic appliance having a hardenable or hardened dental composition of the present invention on the base thereof are illustrated in FIGS. 1-6. It should be noted that for such embodiments, a practitioner can apply the hardenable dental composition to the base of the orthodontic appliance, and then optionally harden the composition. Alternatively, an orthodontic appliance having a hardenable (or hardened) dental composition on the base thereof can be supplied, for example, by a manufacturer, as a "precoated" orthodontic appliance. In yet other embodiments, a practitioner can apply a hardenable dental composition (e.g., an orthodontic primer) to a tooth structure, optionally harden the composition, and then adhere the orthodontic appliance (typically having a hardenable orthodontic adhesive thereon) to the tooth structure.

Figure 2:
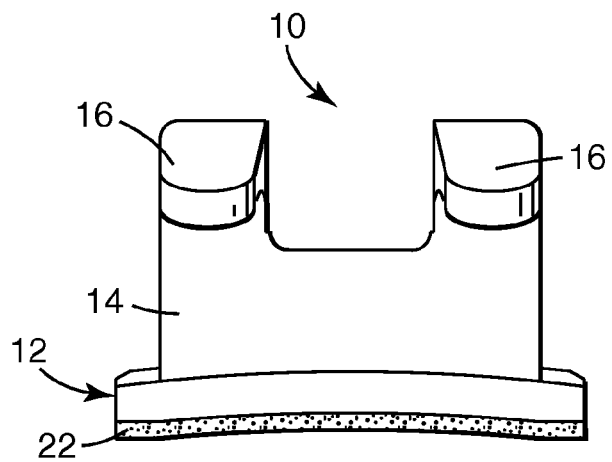
FIG. 2 is a side view of the orthodontic appliance of FIG. 1.

In FIGS. 1 and 2, an exemplary orthodontic appliance is designated by the numeral 10 and is a bracket, although other appliances such as buccal tubes, buttons and other attachments are also possible. The appliance 10 includes a base 12. The appliance 10 also has a body 14 that extends outwardly from the base 12. Base 12 can be a flange made of metal, plastic, ceramic, and combinations thereof. Base 12 can include a mesh-like structure, such as a fine wire screen. Base 12 can include particles (such as shards, grit, spheres, or other structure that optionally includes undercuts). Alternatively, the base 12 can be a custom base formed from one or more hardened dental composition layer(s) (e.g., hardened dental compositions of the present invention, hardened orthodontic adhesives, hardened orthodontic primers, or combinations thereof). Tiewings 16 are connected to the body 14, and an archwire slot 18 extends through a space between the tiewings 16. The base 12, the body 14, and tiewings 16 may be made of any one of a number of materials suitable for use in the oral cavity and having sufficient strength to withstand the correction forces applied during treatment. Suitable materials include, for example, metallic materials (such as stainless steel), ceramic materials (such as monocrystalline or polycrystalline alumina), and plastic materials (such as fiber-reinforced polycarbonate). Optionally, the base 12, the body 14, and the tiewings 16 are integrally made as a unitary component.

Figure 4:
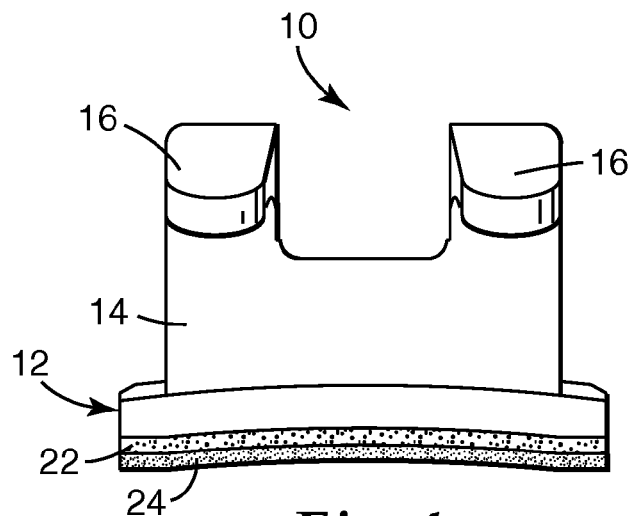
FIGS. 4-6 are side views of orthodontic appliances having a plurality of layers on the bases thereof, in which at least one layer of the plurality of layers is a hardenable or hardened dental composition of the present invention.
Figure 5:
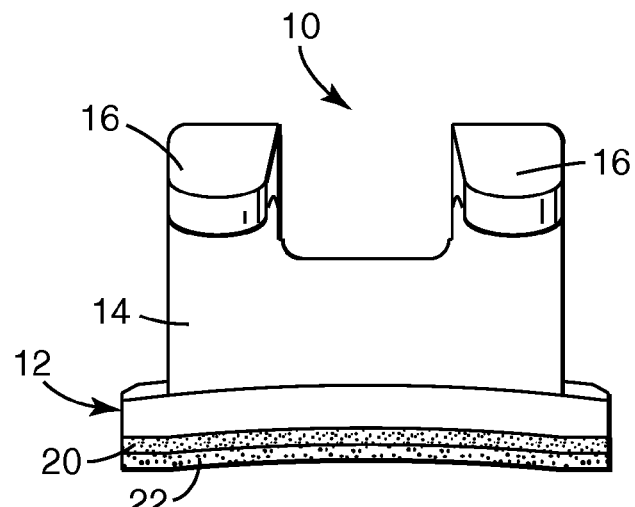
Figure 6:
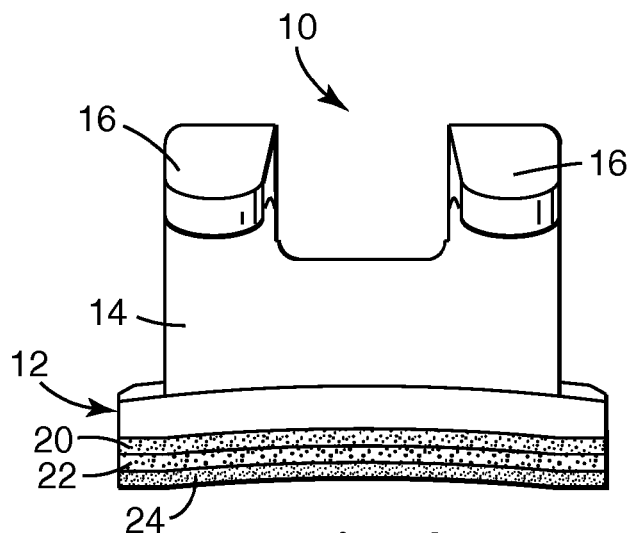

In the exemplary embodiment illustrated in FIGS. 1 and 2, a layer of a hardenable or hardened dental composition of the present invention 22 (hereinafter "composition layer 22"), which is typically an orthodontic adhesive, an orthodontic primer, or an orthodontic sealant, extends across the base 12 of the appliance 10. The composition layer 22 can serve in whole or at least in part to securely fix the appliance 10 to the patient's tooth by a bond having sufficient strength to resist unintended detachment from the tooth during the course of treatment. In one embodiment, the composition layer 22 is applied by the manufacturer to the base 12 of the appliance 10. It should be understood that orthodontic appliance 10 can optionally include additional layer(s) of dental compositions (e.g., orthodontic adhesives, orthodontic primers, or combinations thereof, which are not illustrated in FIGS. 1 and 2) in contact with composition layer 22. Specifically, such additional layer(s) can be between base 12 and composition layer 22; on composition layer 22 opposite base 12; or both. Such layers may or may not cover the same area, and may independently be discontinuous (e.g., a patterned layer) or continuous (e.g., non-patterned) materials extending across all or a portion of adhesive 22. Exemplary appliances including such additional layer(s) are illustrated in FIGS. 4-6.

Orthodontic appliances including multiple hardenable or hardened dental composition layers as described herein can be prepared by methods known to one of skill in the art. Suitable methods include, for example, applying, dispensing, or printing the layers of composition on an appliance or a substrate. Multiple layers may be applied simultaneously or sequentially.

A useful method for applying multiple layers of hardenable dental composition(s) on an orthodontic appliance or a substrate includes, for example, using automated fluid dispensing systems such as those available under the trade designation AUTOMOVE from Asymtek (Carlsbad, Calif.). Such automated fluid dispensing systems are useful for dispensing both patterned and non-patterned layers. Other useful systems include, for example, piston dispensing systems and multiple resolution fluid applicators as described, for example, in U.S. Pat. No. 6,513,897 (Tokie) and U.S. Pat. Application Publication No. 2005/0136370 A1 (Brennan et al.).

Once the hardenable dental composition layer(s) have been applied to an orthodontic appliance or a substrate, the appliance or substrate can conveniently be packaged in a container. Exemplary containers are well known in the art and are disclosed, for example, in U.S. Pat. Nos. 5,172,809 (Jacobs et al.) and 6,089,861 (Kelly et al.).

Figure 3:
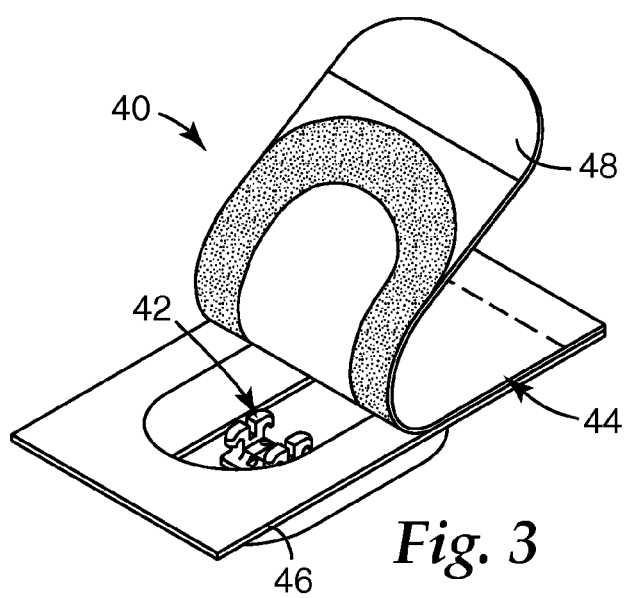
FIG. 3 is a perspective view of a packaged article illustrating an orthodontic appliance having a hardenable or hardened dental composition of the present invention on the base thereof in a container in which the cover has been partially opened.

Referring to FIG. 3, an exemplary embodiment of packaged article 40 including orthodontic appliance 42 having hardenable dental composition layer(s) coated on the base thereof is shown. Package 44 includes container 46 and cover 48. Cover 48, which is releasably connected to container 46 as initially provided, is peeled from container 46 to open the package for removal of orthodontic appliance 42. In FIG. 3, cover 48 has been peeled back from container 46 to partially open package 44.

In preferred embodiments, the package provides excellent protection against degradation of the hardenable dental composition(s) (e.g., photocurable materials), even after extended periods of time. Such containers are particularly useful for protecting dyes that impart a color changing feature to the adhesive. Such containers preferably effectively block the passage of actinic radiation over a broad spectral range, and as a result, the compositions do not prematurely lose color during storage.

In preferred embodiments, the package includes container 46 comprising a polymer and metallic particles. As an example, container 46 may be made of polypropylene that is compounded with aluminum filler or receives an aluminum powder coating as disclosed, for example, in U.S. Pat. Application Publication No. 2003/0196914 A1 (Tzou et al.). The combination of polymer and metallic particles provides a highly effective block to the passage of actinic radiation to color changing dyes, even though such dyes are known to be highly sensitive to light. Such containers also exhibit good vapor barrier properties. As a result, the rheological characteristics of the hardenable dental composition(s) are less likely to change over extended periods of time. For example, the improved vapor barrier properties of such containers provide substantial protection against degradation of the handling characteristics of adhesives so that the compositions do not prematurely cure or dry or become otherwise unsatisfactory. Suitable covers 48 for such containers can be made of any material that is substantially opaque to the transmission of actinic radiation so that the compositions do not prematurely cure. Examples of suitable materials for cover 48 include laminates of aluminum foil and polymers. For example, the laminate may comprise a layer of polyethyleneterephthalate, adhesive, aluminum foil, adhesive and oriented polypropylene.

In some embodiments, a packaged orthodontic appliance including a hardenable dental composition of the present invention thereon may include a release substrate as described, for example, in U.S. Pat. No. 6,183,249 (Brennan et al.).

In other embodiments, a packaged orthodontic appliance including a hardenable dental composition of the present invention thereon may not include a release substrate. In one embodiment, the package includes a substrate with at least one recess with an interior surface. The package includes a means for positioning the orthodontic appliance inside the recess such that the composition layer(s) do not separate from the appliance upon removal of the appliance from the recess. Preferably, the package further includes a cover for the recess and a means for maintaining the cover in contact with the substrate, wherein the means for positioning the orthodontic appliance includes means suspending the appliance in the recess such that the composition layer(s) do not contact the interior surface of the recess. Such packages are disclosed, for example, in U.S. Pat. No. 5,172,809 (Jacobs et al.).

In another embodiment the orthodontic appliance has a base for bonding the appliance to a tooth structure and a body extending from the base and at least two opposed tiewings extending away from the body. The base and at least one of the tiewings extend past the body in a gingival direction and present a gingival recess. The base and at least one other of the tiewings extend past the body in an occlusal direction and present an occlusal recess. The package includes a carrier having a pair of arms extending toward each other. Each of the arms has an outer end section, with the outer end sections being spaced apart from each other and presenting a channel therebetween. The orthodontic appliance is located in the channel and is supported by the arms with one of the outer end sections extending into the occlusal recess and the other of the outer end sections extending into the gingival recess. Such orthodontic appliances and packages are described, for example, in U.S. Pat. No. 6,089,861 (Kelly et al.).

In some embodiments, a packaged article can include a set of orthodontic appliances, wherein at least one of the appliances has a hardenable dental composition of the present invention thereon. Additional examples of articles and sets of appliances are described in U.S. Pat. Application Publication No. 2005/0133384 A1 (Cinader et al.). Packaged orthodontic appliances are described, for example, in U.S. Pat. Application Publication No. 2003/0196914 A1 (Tzou et al.) and U.S. Pat. Nos. 4,978,007 (Jacobs et al.), 5,015,180 (Randklev), 5,328,363 (Chester et al.), and 6,183,249 (Brennan et al.).

An orthodontic appliance having a hardenable dental composition of the present on the base thereof may be bonded to a tooth structure using methods (e.g., direct or indirect bonding methods) that are well known in the art. Upon application of the orthodontic appliance to the tooth structure, the hardenable dental composition of the present invention can be hardened to adhere the orthodontic appliance to the tooth structure. A variety of suitable methods of hardening the composition are known in the art. For example, in some embodiments the hardenable dental composition can be hardened by exposure to UV or visible light. In other embodiments, the hardenable dental composition can be provided as a multi-part composition that hardens upon combining the two or more parts.

When desired, typically upon completion of the orthodontic treatment process, the practitioner needs to remove the orthodontic appliance from the tooth structure. Hardened dental compositions of the present invention are designed to increase in temperature upon irradiation, which typically reduces the bond strength to allow for convenient removal of not only the orthodontic appliance, but also for removal of any hardened dental composition remaining on the tooth structure after removal of the appliance.

The hardened dental composition can be heated by irradiation with radiation that is absorbed by the radiation-to-heat converter. A wide variety of radiation sources can be used including, for example, lasers, laser diodes, quartz-tungsten-halogen lamps, mercury lamps, doped mercury lamps, deuterium lamps, plasma arc lamps, LED sources, and other sources known in the art.

The hardened dental composition can irradiated for a time sufficient to heat the hardened dental composition to a temperature sufficient to decrease the bond strength and allow for convenient removal of the orthodontic appliance from the tooth structure. Preferably the temperature and time are chosen to prevent damage to the tooth structure as described, for example, in Zach et al. in "Endodontics," Bender, Editor, pp. 515-530 (1965). See, also, Laufer et al., *Journal of Biomechanical Engineering*, 107:234-239 (1985); Launay et al., *Lasers in Surgery and Medicine*, 7:473-477 (1987); Azzeh et al., *American Journal of Orthodontics and Dentofacial Orthopedics*, 123:79-83 (2003); and Uysal et al., *Angle Orthodontist*, 75:220-225 (2005). Typically, by using irradiation conditions that result in rapid heating of the dental composition, higher temperatures can be achieved for shorter durations without damaging the tooth structure.

In certain embodiments, at least a portion, and preferably all, of the hardened dental composition, is irradiated to heat the composition to at least 42° C., sometimes at least 50° C., and other times at least 70° C. Typically, the hardened dental composition is irradiated to heat the composition to at most 200° C., sometimes at most 150° C., other times to at most 100° C., and even other times to at most 80° C. The selected temperature is maintained for a time sufficient to result in the desired decrease in bond strength. In certain embodiments, the time is at most 10 minutes, sometimes at most 10 seconds, and other times at most 1 second. The decrease in bond strength typically results in fracture within the hardened composition layer.

In some embodiments, the orthodontic appliance includes an additional dental composition layer. Such additional dental composition layers can include, for example, unhardened or hardened dental compositions (e.g., in certain embodiments, a conventional dental composition not including a radiation-to-heat converter). The inclusion of additional layers can influence, for example, where fracture takes place during debonding of the orthodontic appliance from the tooth structure, as described herein below.

For example, FIG. 4 illustrates an embodiment in which orthodontic appliance 10 has one additional dental composition layer 24 in contact with composition layer 22. Composition layer 22 may be either an unhardened or hardened dental composition of the present invention. Additional layer 24 is on composition layer 22 opposite base 12. Additional layer 24 is typically an unhardened dental composition (e.g., an orthodontic adhesive, an orthodontic primer, or a combination thereof). Upon application of orthodontic appliance 10 to a tooth structure, additional layer 24 (and composition layer 22 if not already hardened) can be hardened by a variety of methods as described herein above to adhere the orthodontic appliance to the tooth structure.

In some embodiments, additional layer 24 can be a hardenable orthodontic primer that is coated on the tooth structure (and optionally hardened) before the orthodontic appliance with composition layer 22 thereon is adhered to the tooth surface.

Upon completion of the orthodontic treatment, at least a portion of hardened composition layer 22 can be irradiated to heat the composition and reduce the bond strength, and preferably allow fracture within heated composition layer 22 upon removal of the orthodontic appliance. Fracture within heated composition layer 22 results in fracture near the orthodontic appliance and away from the tooth structure. Further, the heated, hardened composition layer 22 (e.g., an orthodontic adhesive) typically has a lower modulus, and therefore is softer to allow for easier cleanup and/or removal of any remnants of the hardened composition. Therefore, after orthodontic treatment, one embodiment of FIG. 4 would be where composition layer 22 and additional layer 24 are both hardened orthodontic adhesives. In another embodiment, composition layer 22 would be a hardened orthodontic adhesive and additional layer 24 would be a hardened orthodontic primer.

FIG. 5 illustrates another embodiment in which orthodontic appliance 10 has one additional dental composition layer 20 in contact with composition layer 22. Additional layer 20 is between base 12 and composition layer 22. Additional layer 20 is typically an unhardened or hardened dental composition (e.g., an orthodontic adhesive, an orthodontic primer, or a combination thereof). Composition layer 22 is typically unhardened. Upon application of orthodontic appliance 10 to a tooth structure, composition layer 22 (and additional layer 20 if not already hardened) can be hardened by a variety of methods as described herein above to adhere the orthodontic appliance to the tooth structure.

In some embodiments, composition layer 22 can be a hardenable orthodontic primer that is coated on the tooth structure (and optionally hardened) before the orthodontic appliance with additional layer 20 thereon is adhered to the tooth surface.

Upon completion of the orthodontic treatment, at least a portion of hardened composition layer 22 can be irradiated to heat the composition and reduce the bond strength, and preferably allow fracture within heated composition layer 22 upon removal of the orthodontic appliance. Fracture within heated composition layer 22 results in fracture near the tooth structure. For embodiments in which composition layer 22 is an orthodontic primer and additional layer 20 is an orthodontic adhesive, the hardened orthodontic adhesive is substantially retained on the removed orthodontic appliance. As used herein, "substantially retained on the removed orthodontic appliance" means that at least 50% by weight, and preferably at least 75% by weight of the orthodontic adhesive is retained on the removed orthodontic appliance. When the hardened orthodontic adhesive is substantially retained on the removed orthodontic appliance, clean up and removal of any adhesive remaining on the tooth structure is more convenient, because less adhesive remains on the tooth structure. Additionally, any composition remaining on the tooth structure is preferably substantially the hardened dental composition of the present invention, which can optionally be heated to soften the composition, and thereby allow for easier adhesive removal. Therefore, after orthodontic treatment, one embodiment of FIG. 5 would be where composition layer 22 and additional layer 20 are both hardened orthodontic adhesives. In another embodiment, composition layer 22 would be a hardened orthodontic primer and additional layer 20 would be a hardened orthodontic adhesive.

For another example, FIG. 6 illustrates an embodiment in which orthodontic appliance 10 has two additional dental composition layers (20 and 24) in contact with composition layer 22. Additional layer 20 is between base 12 and composition layer 22. Additional layer 20 is typically an unhardened or hardened dental composition (e.g., an orthodontic adhesive, an orthodontic primer, or a combination thereof). Composition layer 22 can be unhardened or hardened. Additional layer 24 is on composition layer 22 opposite base 12. Additional layer 24 is typically an unhardened dental composition (e.g., an orthodontic adhesive, an orthodontic primer, or a combination thereof). Upon application of orthodontic appliance 10 to a tooth structure, additional layer 24 (and composition layer 22 and additional layer 20, if not already hardened) can be hardened by a variety of methods as described herein above to adhere the orthodontic appliance to the tooth structure.

In some embodiments, additional layer 24 can be a hardenable orthodontic primer that is coated on the tooth structure (and optionally hardened) before the orthodontic appliance with additional layer 20 and composition layer 22 thereon is adhered to the tooth surface.

Upon completion of the orthodontic treatment, at least a portion of hardened composition layer 22 can be irradiated to heat the composition and reduce the bond strength, and preferably allow fracture within heated composition layer 22 upon removal of the orthodontic appliance. Fracture within heated composition layer 22 results in fracture between, yet safely away from, the orthodontic appliance and the tooth structure. Therefore, after orthodontic treatment, one embodiment of FIG. 6 would be where composition layer 22 and additional layers 20 and 24 are all hardened orthodontic adhesives. In another embodiment, composition layer 22 would be a hardened orthodontic adhesive and additional layers 20 and 24 would be hardened orthodontic primers.

It is to be understood that additional embodiments are contemplated in which additional layers or arrangements of layers are present. Further, the thickness of each layer can be individually varied as desired. Further, dental compositions of the present invention need not be present only in explicitly defined layers, but can also be present distributed uniformly or non-uniformly throughout all or a portion of the layer(s) present on the base of the orthodontic appliance. In some cases a high concentration of a radiation-to-heat converter may be applied as a particulate layer directly to a hardenable dental composition containing the radiation-to-heat converter or to a conventional dental composition not including a radiation-to-heat converter. Further, a thin layer (e.g., a primer) may optionally be applied to the particulate surface to enhance wetting of the tooth upon application of the appliance.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Shear Bond Strength on Glass Test Method A

Bond strengths of orthodontic brackets adhered to glass with adhesive test samples were measured with an Instron Model R5500 universal testing machine fitted with an Instron Model 2511-111 500 N load cell (Instron Corp., Canton, Mass.). The crosshead speed was 0.5 cm/min and 10 data points were collected each second. Window glass coupons (15 cm×2.54 cm×0.30 cm) were cleaned with methanol and allowed to dry at room temperature for 5 minutes. Orthodontic brackets (TRANSCEND 6000, 3M Unitek) were adhered to the window glass coupons using an adhesive as described in the subsequent Examples. Curing was done photochemically with a Super Spot Max fiber optic 100 W Hg—Xe light source (Lesco, Torrance, Calif.) fitted with a 300-nm long pass optical filter. The glass slides with attached brackets were fastened to the Instron crosshead in a clamped mold. An orthodontic standard round wire (0.51 mm, Part number 211-200, 3M Unitek, Monrovia, Calif.) that was clamped to the load cell was passed through the bottom of the bracket such that the brackets were debonded in shear once the crosshead was moved. Prior to debonding (i.e., shearing off the glass surface), the cured adhesives were irradiated for 20 seconds through the brackets with a 75 W QTH blue light gun (Litema Astral Dental, Baden-Baden, Germany) with its dichromic mirror removed. The light gun was gently placed against the bracket surface during the irradiation and the irradiation was continued after the load frame was in motion until debonding occurred. The maximum stress required to debond the bracket was reported in force per unit area (MPa). Each experiment was repeated typically 3 to 10 times.

Shear Bond Strength on Teeth Test Method A

Bond strengths of orthodontic brackets adhered to teeth with adhesive test samples were determined by the following method. Approximately 10 mg of the adhesive test sample was applied by syringe to the bonding base of a TRANSCEND 6000 (3M Unitek), VICTORY Series (3M Unitek), or CLARITY (3M Unitek) orthodontic bracket. One bracket type would be glass/grit-coated CLARITY Bracket (REF 6400-601 or equivalent; 3M Unitek). The bovine teeth were potted in a fast curing poly(methyl methacrylate) base. The teeth were then cleaned with a pumice aqueous slurry and rinsed. The slightly moist teeth were primed/etched with TRANSBOND Plus SEP self-etching primer (3M Unitek) [or with TRANSBOND PLUS SEP self-etching primer filled with 40% by weight TONE P747 (Example 11)—see Evaluations of Bond Strengths for Examples 1-9 and 12-15], and then dried with moisture- and oil-free air. The ceramic bracket with adhesive was then seated onto the tooth and pressed firmly to extrude any excess adhesive. The excess adhesive was cleaned away and then the adhesive-coated bracket was bonded to the tooth via curing with an ORTHOLUX LED Curing light (3M Unitek) for 3 sec though the top of the bracket. The samples of teeth and bonded brackets were stored overnight in water at 37° C. and, if heating was desired, transferred to a water bath at 75° C. for either 2 minutes or for 2 hours. Bond strength testing was performed as follows with the heated samples tested as quickly as possible to avoid heat loss. A 0.50-mm round stainless steel wire loop (e.g., Part number 211-200, 3M Unitek) was engaged under the occlusal tie wings of the bracket. Using a Qtest/5 Tester (MTS Systems), a load was applied in a shear/peel mode until debonding from the tooth occurred. The wire attached to the tester was pulled at a rate of 5 mm/minute. The maximum force (in units of pounds) was recorded as bond strength per bracket and the reported value was an average of 10 measurements using 10 different adhesive coated brackets bonded to teeth. This average was then converted to units of MPa by dividing by the bonding base area (square inches) of the bracket and then multiplying by 0.006895.

Shear Bond Strength on Teeth Test Method B

Bond strengths of ceramic orthodontic brackets adhered to bovine teeth with adhesive test samples were measured with a Qtest/5 Tester (MTS Systems). A load was applied in a shear/peel mode until debonding from the tooth occurred. The crosshead speed was 0.5 cm/min. CLARITY (for example REF 6400-601 or equivalent; 3M Unitek) brackets were silane treated by immersion in SCOTCHPRIME ceramic primer (3M Company) that was diluted with ethanol to 0.5% active silane (standard SCOTCHPRIME contains 1.0% active silane), followed by air-drying and then standing for 1 hour in a 600° C. oven. After cooling to room temperature, the brackets were again immersed in SCOTCHPRIME ceramic primer diluted to 0.5% active silane as above followed by air-drying and then standing in a 100° C. oven for 1 hour. The brackets were allowed to cool to room temperature. Approximately 10 mg of the adhesive test sample was applied by syringe to the bonding base of the silane-treated CLARITY bracket. The bovine teeth were potted in a fast curing poly(methylmethacrylate) base. The teeth were then cleaned with a pumice aqueous slurry and rinsed.

TRANSBOND PLUS SEP self-etching primer (3M Unitek) was applied to the slightly moist bovine teeth and dried with an air jet. Thereafter, the adhesive pre-coated CLARITY brackets were placed on the teeth, excess flash removed and the brackets were cured for 5 seconds with an ORTHOLUX LED Curing light (3M Unitek) to adhere the brackets to the teeth. The specimens were stored at 37° C. for 24 hours and then sheared on the Instron using a Qtest/5 Tester (MTS Systems) as described in Shear Bond Strength on Teeth Method A above. Immediately prior to shear loading the test specimens, they were irradiated with an ORTHOLUX XT QTH light source (3M Unitek) with its IR reflective mirror removed so that it emitted NIR radiation as well as white light. The irradiation was conducted for 60 seconds followed by activation of the load frame on the Qtest/5 Tester with continued irradiation until debonding occurred. The maximum force (in units of pounds) was recorded as bond strength per bracket and the reported value was an average of 5 measurements. This average was then converted to units of MPa by dividing by the bonding base area (square inches) of the bracket and then multiplying by 0.006895.

Shear Bond Strength on Teeth Test Method C

Orthodontic brackets were bonded to bovine teeth surfaces by a photo bonding procedure and then about half the samples were subjected to UVA light irradiation for debonding as described in Examples 16 and 17. For debonding, all the samples were subjected to a 20-second irradiation period with a modified Litema Astral light gun (Litema Dental, Baden-Baden, Germany) with its internal blue light metallized filter removed. During the irradiation period, the light gun was gently pressed against the top of the bonded bracket and the temperature of the adhesive layer (containing the near infrared (NIR) absorber TRB SH 7080) increased to about 100° C. Immediately after irradiation, the UVA light-irradiated bonded brackets (plus the non-UVA-irradiated bonded bracket control sample) were sheared off of the teeth surfaces using an Instron R5500 instrument (Instron Corp., Canton, Mass.) equipped with a 500-N load cell. Strain was applied at 0.5 cm/min and data were collected at 10 dpts/second. Data were reported in lb-f units and then converted to a force per unit area (MPa). Each experiment included four to seven replications.

Abbreviations, Descriptions, and Sources of Materials

| Abbreviation | Description and Source of Material |
|---|---|
| HEMA | 2-Hydroxyethyl methacrylate (Sigma-Aldrich, St. Louis, MO) |
| BisGMA | 2,2-Bis[4-(2-hydroxy-3-methacryloyloxypropoxy)-phenyl]propane CAS No. 1565-94-2 |
| Diacryl 101 | BisEMA, Bis(2-hydroxyethyl)bisphenol-A-dimethacrylate (Akzo Chemicals, Inc., Chicago, IL) |
| BisEMA6 | Ethoxylated bisphenol A dimethacrylate (Sartomer) |
| PEGDMA-400 | Polyethyleneglycol dimethacrylate (Sartomer 603; MW about 570; Sartomer) |
| CDMA | Citric acid dimethacrylate (See Preparation Method described herein) |
| IRGACURE 819 | Phosphine oxide photoinitiator (Ciba Specialty Chemicals Corp., Terrytown, NY) |
| CPQ | Camphorquinone (Sigma-Aldrich) |
| EDMAB | Ethyl 4-(N,N-dimethylamino)benzoate (Sigma-Aldrich) |
| DPIHFP | Diphenyl Iodonium Hexafluorophosphate (Johnson Matthey, Alpha Aesar Division, Ward Hill, NJ) |
| BHT | 2,6-di-tert-butyl-4-methylphenol (Sigma-Aldrich) |
| EYB | Erythrosin Yellowish Blend Dye (Blend of 90/10 by weight Erythrosin dye to Eosin Y dye) (Sigma-Aldrich) |
| DBTDL | Dibutyltin dilaurate (Sigma-Aldrich) |
| TPS | Triphenylantimony (Sigma-Aldrich) |
| TRB SH 7080 | Blue-colored sol containing indium-tin-oxide (ITO) nanoparticles (40 wt.-%) in methyl cellosolve (40 wt.-%) and a urethane acrylate (20 wt.-%). An efficient NIR-absorber. (Advanced NanoProducts, S. Korea) |
| NANOTEK 0600 ITO | Yellow-green indium-tin-oxide (ITO) powder. An efficient NIR-absorber. (Nanophase, Romeoville, IL) |
| EPOLIGHT 2057 | Soluble dye known as an efficient NIR-absorber. (Epolin, Inc., Newark, NJ) |
| EFKA 4400 | Acrylic polymer dispersant (EFKA, Heerenveen, Netherlands) |
| TONE P767 | Poly(caprolactone) (PCL; Union Carbide, Charleston, WV) In certain cases, as indicated in specific Examples, the TONE P767 was finely ground with mortar and pestle prior to use. |
| QPAC-40 | Poly(propylene carbonate) (PPC; Empower Materials Inc., Newark, DE) |
| DBU | Diazabicyclo[5.4.0]undec-7-ene (AMICURE DBU; Air Products; Wayne, PA |
| APC PLUS | Orthodontic Adhesive (3M Unitek, Monrovia, CA) |
| SCOTCH-PRIME | Silane-containing solution (1.0%) also available as 3M ESPE RELY-X Ceramic Primer (3M Company) |
| BHA | Behenyl acrylate (Cognis, Cincinnati, OH) |
| VAZO 67 | Thermal initiator (DuPont, Wilmington, DE) |
| IEM | 2-Isocyanatoethyl methacrylate (Sigma-Aldrich) or (Kowa American Corp., New York, NY) |
| t-BOCDMA | "Tertiary-butyloxycarbonyl 2-hydroxyethyl dimethacrylate" (See preparation method and chemical structure described herein.) |
| CHDVE | Cyclohexyl divinyl ether (1,4-bis(vinyloxymethyl)-cyclohexane), (International Specialty Products, Wayne, NJ) |
| CHDVEDMA | Cyclohexyl divinyl ether dimethacrylate (1,4-bis(α-(methacryloyloxyethyloxymethyl)cyclohexane); see preparation method and chemical structure described herein. |
| $Ar_3S^+PF_6^-$ | Triaryl sulfonium hexafluorophosphate, Cyracure CPI-6992, 50% solution in propylene carbonate (Aceto Corp., Lake Success, NY) |
| SO-E2 Filler | Silica Powder; average particle size = 500 nm (Tatsumori Limited, Tokyo, Japan) |
| Filler A | "Control Glass" as described in Example 1 of U.S. Pat. No. 5,154,762 (Mitra et al.) and subsequently silane-treated as described for Filler FAS I in U.S. Pat. Publication No. 2003/0166740 (Mitra et al.). Average particle size estimated to be 3.0 micrometers. |
| Filler B | Fluoroaluminosilicate Schott glass filler (particle size about 1 micrometer); silane-treated with A174 silane (OSI Specialties, West Charleston, WV) |
| Filler C | CAB-O-SIL TS-720 (Cabot Corp.) - Fumed (pyrogenic) silica surface treated with dimethylsilicone |
| Filler E | Blend of Filler A (49.2 wt.-%), Filler B (49.2 wt.-%), and Filler C, (1.6 wt.-%) |

Starting Materials Preparations

Resins A, B, C and D

Resins A, B, C and D were prepared by combining the ingredients as shown in Table 1. Resins C and D were prepared by combining the ingredients as shown in Table 1 and heating the resulting mixture to 50-60° C. for 10 to 15 minutes.

TABLE 1

Compositions of Resins A, B, C and D

| Ingredient (Weight %) | Resin A Transbond XT | Resin B APC Plus (CESSNA) | Resin C From AA-1087 | Resin D From CRML-1094 |
|---|---|---|---|---|
| HEMA | 0 | 0 | 89.6 | 0 |
| BisGMA | 59.53 | 5.61 | 9.5 | 5.6 |
| CDMA/PEGDMA-400 (1:1) | 0 | 79.16 | 0 | 0 |
| CDMA | 0 | 0 | 0 | 39.6 |
| Diacryl 101 | 38.52 | 0 | 0 | 0 |
| PEGDMA-400 | 0 | 11.22 | 0 | 50.8 |
| IRGACURE 819 | 0 | 0 | 0.9 | 0 |
| BHT | 0.10 | 0.50 | 0 | 0.50 |
| CPQ | 0.25 | 0.50 | 0 | 0.50 |
| EDMAB | 1.00 | 2.25 | 0 | 2.25 |
| DPIHFP | 0.60 | 0.75 | 0 | 0.75 |
| EYB | 0 | 0.03 | 0 | 0.025 |
| TOTAL: | 100 | 100 | 100 | 100 |

Preparation of CDMA

In a reaction vessel fitted with a mechanical stirrer, condenser, addition funnel, and air inlet tube, 400 g of citric acid was dissolved in 2 liters of dry THF. To the resultant homogeneous solution was added 0.52 g BHT, 0.5 g TPS, and 0.98 g DBTDL. Dry air was added to the reaction mixture through the inlet tube. Then, 161.5 g (1.04 moles) of IEM was added dropwise through the addition funnel so as to maintain a reaction temperature of about 40° C. The reaction was followed by infrared spectroscopy. After all of the IEM had been added and the IR spectrum showed little to no isocyanate group, the THF was removed under vacuum from the reaction mixture. The resultant viscous liquid was dried. Nuclear magnetic resonance spectroscopy showed the presence of added methacrylate groups and the retention of carboxy groups.

Preparation of t-BOCDMA

Figure 7:
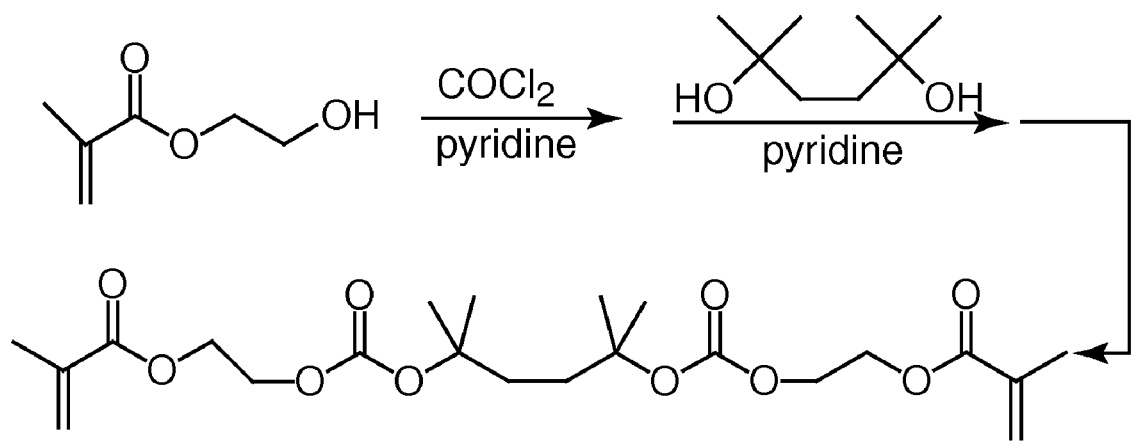
FIG. 7 is a schematic representation of an exemplary method for preparing tertiary-butyloxycarbonyl 2-hydroxyethyl dimethacrylate (t-BOCDMA) as described herein.

A schematic representation of an exemplary method for preparing t-BOCDMA is illustrated in FIG. 7. In brief, 2-(chloroformyl)ethyl methacrylate, either isolated or prepared in situ, is allowed to react with 2,5-dimethylhexane-2,5-diol as described herein below.

Synthesis and isolation of 2-(chloroformyl)ethyl methacrylate. A solution of HEMA (7.24 g) and dry pyridine (6.5 ml, distilled from calcium hydride) was prepared in dry toluene (50 ml, JT Baker) by stirring under nitrogen in an ice bath. To this solution was added dropwise a solution of phosgene in toluene (36 ml, Sigma-Aldrich) with stirring. A colorless precipitate formed immediately. The mixture was stirred for two hours and vacuum filtered in a fume hood to yield a colorless filtrate. The filtrate was evaporated to dryness using a rotary evaporator in a fume hood to yield a pale yellow oil. The oil was further dried using a vacuum pump (<5 Torr). The yield was 6.35 g and the structure was determined by proton NMR to be 2-(chloroformyl)ethyl methacrylate.

Synthesis and purification of the mono methacrylate ester (Compound A) derived from the reaction of 2-(chloroformyl)

ethyl methacrylate (prepared in situ from triphosgene and HEMA) and 2,5-dimethylhexane-2,5-diol. A solution of triphosgene (3.91, Sigma-Aldrich) in methylene chloride (150 ml, JT Baker) was prepared under nitrogen in an ice bath with stirring. Dry pyridine (3.2 ml, distilled from calcium hydride) was added dropwise to the solution with stirring. An exothermic reaction occurred and the solution turned yellow with some precipitation. After stirring for 30 minutes the solution turned clear yellow. The solution was cooled in an ice bath and HEMA (5.11 g) in methylene chloride (10 ml) was added dropwise. After stirring for 30 minutes, another 3.2 ml of dry pyridine was added dropwise immediately followed by the addition of 2,5-dimethylhexane-2,5-diol (2.87 g, Sigma-Aldrich). The resultant pale yellow solution was stirred for 30 minutes followed by stripping of the solvent using a rotary evaporator. The resultant pasty yellow mixture was stirred in toluene (100 ml) for 1 hour in air and vacuum filtered. Rotary evaporation yielded a yellow oil that was purified by liquid chromatography ($SiO_2$, hexanes:ethyl acetate 10 to 35% gradient) to yield Compound A (3.05 g). The structure of Compound A was determined by proton NMR to be the 2-hydroxy 5-mono(methacrylate ester) reaction product of 2-(chloroformyl)ethyl methacrylate and 2,5-dimethylhexane-2,5-diol.

Synthesis and purification of t-BOCDMA. A solution of Compound A (4.60 g) and dry pyridine (1.7 ml, distilled from calcium hydride) was prepared in dry toluene (50 ml, JT Baker) by stirring under nitrogen in an ice bath. 2-(Chloroformyl)ethyl methacrylate (3.25 g) was added dropwise to the solution with stirring. The resultant mixture was vacuum filtered after 2 hours using CELITE as a filter aid. The filtrate was rotary evaporated to yield a nearly colorless oil that was stabilized with 30 ppm of tris(N-nitroso-N-isopropylhydroxylaminato)aluminum (NPAL, Albemarle, Baton Rouge, La.). The oil was purified by repeated liquid chromatography ($SiO_2$, hexanes:ethyl acetate 10 to 35% gradient followed by $SiO_2$ with methylene chloride:methanol 0 to 5% gradient). The yield of t-BOCDMA was 1.35 g. The structure of t-BOCDMA (shown above) was determined by proton NMR to be the 2,5-bis(methacrylate ester) reaction product of 2-(chloroformyl)ethyl methacrylate and Compound A.

Preparation of CHDVEDMA

Figure 8:
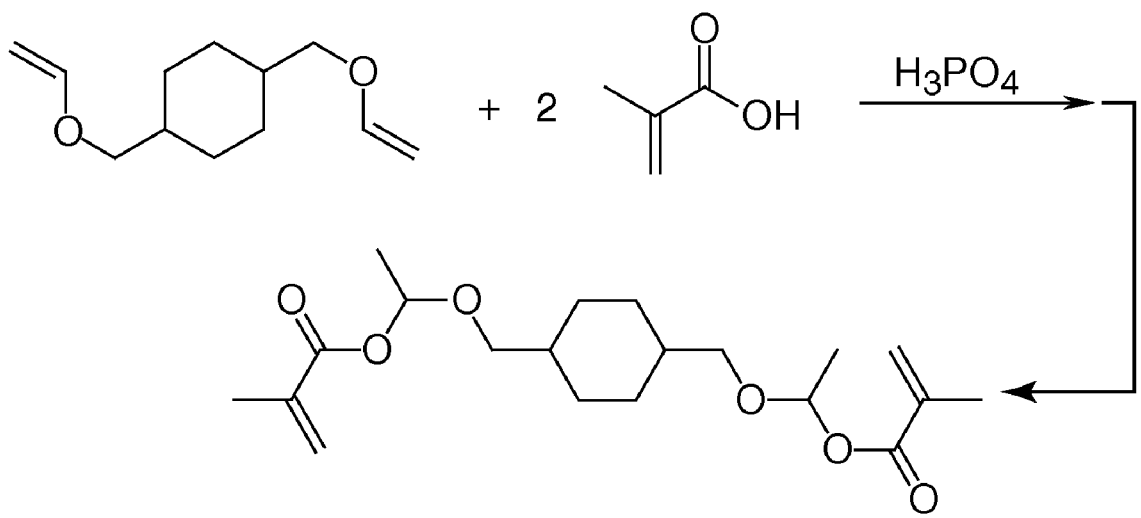
FIG. 8 is a schematic representation of an exemplary method for preparing cyclohexyl divinyl ether dimethacrylate (CHDVEDMA) as described herein.

A schematic representation of an exemplary method for preparing CHDVEDMA is illustrated in FIG. 8. In brief, cyclohexyl divinyl ether is allowed to react with methacrylic acid as described herein below.

Synthesis and purification of CHDVEDMA. A mixture of methacrylic acid (12.17 g, Sigma-Aldrich) and CHDVE (25.00 g) was prepared in a 250-ml round bottom flask equipped with a magnetic stirrer and an ice bath. A drop of phosphoric acid (JT Baker) was added to the mixture and the mixture stirred for 3 hours and allowed to attain room temperature spontaneously. After 3 hours of stirring, an additional 10.89 gm of methacrylic acid was added. The resulting mixture was stirred overnight under nitrogen. Finely ground anhydrous potassium carbonate (10.09 g, JT Baker) was then added and the resulting mixture stirred for 2 hours at room temperature. A thick, colorless suspension resulted that was taken up in anhydrous ethyl acetate (JT Baker) and filtered through a CELITE filter pad and subsequently through a 4-8 μm porosity glass frit (Ace Glass) to yield a colorless solution with a slight haze to it. Tris(N-nitroso-N-phenyl hydroxylamine)aluminum (4.8 mg, Albemarle, Baton Rouge, La.) was added to the solution and the solvent removed on a rotary evaporator at less than 10° C. A colorless oil was recovered with a yield of 41.1 gm. The structure of CHDVEDMA (shown above) was confirmed by proton NMR.

Preparation of Polycaprolactone (PCL) Fibers and Polypropylene Carbonate (PPC)

Electrospinning Solution A. Preparation of 20% w/v Solution of TONE P767E (PCL) in Methyl Ethyl Ketone (MEK): To a 237-ml glass jar was added 80 ml of MEK, and the height of the solvent was marked with a felt-tipped pen on the outside of the jar. The MEK was removed from the jar and TONE P767E (PCL; 16 g) was added. MEK was added back to the jar, up to the marked level. A layer of PTFE tape was placed on the threads of the jar, and a metal-lined metal lid was screwed on tightly by hand. The closed jar was placed onto a shaker table (Eberbach, Ann Arbor, Mich.) and heated with two, 250-Watt IR heat lamps (General Electric), each connected to a rheostat (Staco Energy Products, Dayton, Ohio) at setting of 80-85%. After shaking for 2 hours, the PCL had dissolved in the MEK to afford Electrospinning Solution A that was ready for electrospinning into fibers as described below. A thermocouple was used on the outside of the bottle during the heating, with a reading of 80° C. observed.

Electrospinning Solution B. Preparation of 20% w/v Solution of QPAC-40 (PPC) in MEK: To a 473-ml glass jar was added 100 ml of MEK, and the height of the solvent was marked with a felt-tipped pen on the outside of the jar. The MEK was removed from the jar and QPAC-40 (PPC; 20 g) was added. MEK was added back to the jar, up to the marked level. A layer of PTFE tape was placed on the threads of the jar, and a metal-lined metal lid was screwed on tightly by hand. The closed jar was placed onto a shaker table (Eberbach) and heated with two, 250-Watt IR heat lamps (General Electric), each connected to a rheostat (Staco Energy Products) at setting of 80-85%. After shaking for 3 hours, the PPC had dissolved in the MEK to afford Electrospinning Solution B that was ready for electrospinning into fibers as described below. A thermocouple was used on the outside of the bottle during the heating, with a reading of 80° C. observed.

Electrospinning process: An electrospinning apparatus was prepared using a disposable 60-ml syringe (Beckton-Dickinson, Rutherforsd, N.J.) and a blunt, stainless steel syringe tip (EFD, East Providence, R.I.), attached to a syringe pump (Orion Sage M365, Thermo Electron Corp., Beverly, Mass.). An aluminum panel (0.6 mm×76.2 mm×127 mm; Q-Panel Co., Cleveland, Ohio), that had a small hole (1.27 mm diameter) in the center, was slipped over the syringe tip and positioned approximately 20 mm from the syringe tip. A grounded, high-voltage power supply (CZE 1000R, Spellman High Voltage Electronics, Hauppauge, N.Y.) was connected to the syringe tip in front of the aluminum panel.

An aluminum baking sheet (30.5-cm length×20.3-cm width×2.54-cm depth; Pactiv Corp. Lake Forest, Ill.) was used as the ground plane. Glass slides (optionally coated with ITO to give a resistivity of about 600 ohms/square; available from Optera Inc., Holland, Mich.) were attached to the aluminum pan using double-stick tape, and were positioned so that the slides were 20 cm from the syringe tip. After setting the syringe pump to the desired flow rate and setting the power supply to 20 kV, the power supply was activated to deposit the polymer fibers on the glass slide. Each slide was prepared independently, and for the appropriate time as designated in particular experiment.

Figure 9A:
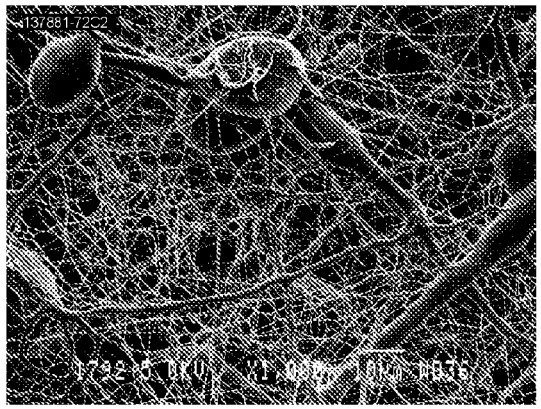
FIG. 9a illustrates scanning electron micrographs of poly (caprolactone) (PCL) nanofibers.
Figure 9B:
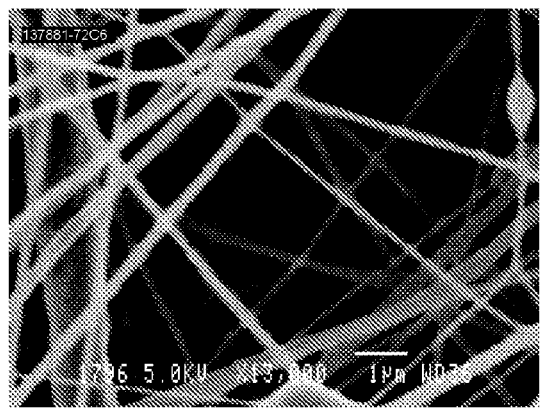

Scanning Electron Microscopy (SEM) of PCL fibers prepared from Electrospinning Solution A using these conditions (10.2 ml/hour flow rate for 90 seconds) showed a random mat of mostly sub-micron fibers with a few fibers having diameters up to 10 microns. Beads are also present on a few of the fibers as shown in FIGS. 9*a-b.*

Preparation of BHA/HEMA-IEM (Behenyl Acrylate/ HEMA-IEM Adduct) Polymer

Into a 250-ml round bottom flask with magnetic stirrer was added BHA (18 g), HEMA (2 g), VAZO 67 (0.06 g), toluene (40 g), and ethyl acetate (40 g). This 20% solids solution was degassed using nitrogen for about 10 minutes, sealed, and immersed in a hot oil bath at 65° C. for 20 hours. A 50-g aliquot of the resulting polymeric solution was added to a 450-ml glass jar. Based on the percent solids and the 2-HEMA content in the polymer, the number of moles of hydroxyl groups was calculated and an equivalent number of moles of IEM were added together with a few drops of DBTDL catalyst. The resulting mixture was allowed to agitate for 12 hours at room temperature. The complete consumption of the isocyanate was confirmed by IR spectroscopy.

After solvent removal, the resulting solid was ball milled in a size 000 porcelain jar with 450 g of 10-mm zirconia media (Tosoh YTZ, Tosoh Corporation, Tokyo, Japan) at 100 rpm for 16 hours in 70 g of isopropanol. The media was separated by decanting to yield a colorless suspension. The solvent was removed by rotary evaporation at 25° C. followed by 0.035 torr vacuum for 2 hours and finally by standing under <1 torr vacuum at 30° C. for 18 hours. A fine colorless powder (designated BHA/HEMA-IEM polymer) was obtained and used without further modification. Particle size analysis was done using a CAPA-700 particle size analyzer (Horiba Corporation, Sunnyvale, Calif.). The powder was resuspended in isopropanol by ultrasonication (VibraCell, Sonics and Materials, Inc., Danbury, Conn.) for 5 minutes. The d50 (median) particle size was determined to be 4.1 micrometers by this method.

Example 1

Indium Tin Oxide (ITO) Dispersed in HEMA

A dispersion of ITO in HEMA was prepared by combining HEMA (70.0 g), EFKA 4400 Dispersant (0.5 g), and NANOTEK 0600 ITO (10.0 g) and ball-milling for 72 hours at 100 rpm in a size 000 porcelain jar with Tosoh 5-mm YTZ grinding media (450 g). Particle size analysis of the resulting yellow dispersion (Example 1) showed the ITO to have an average particle size of 160 nm.

Example 2

Indium Tin Oxide (ITO) Dispersed in Adhesive Resin

A dispersion of ITO in an adhesive resin was prepared by combining Resin B (97 wt.-%) and TRB SH 7080 (3 wt.-%) to provide a dispersion (Example 2) with a 1.2 wt.-% effective concentration of ITO. Upon curing (as a 1-cm diameter disk) with a Model 2500 Dental Blue Lamp (3M Company), the purple-colored monomeric dispersion transformed into a green-colored, transparent polymer.

Example 3

ITO Dispersed in Adhesive Resin

A dispersion of ITO in an adhesive resin was prepared by combining Resin B (78.3 wt.-%) and ITO-HEMA (Example 1; 21.7 wt.-%) to provide a dispersion (Example 3) with a 2.7 wt.-% effective concentration of ITO. Upon curing (as a 1-cm diameter disk) with a Model 2500 Dental Blue Lamp (3M Company), the monomeric dispersion transformed into a yellow, opaque polymer.

Example 4

Polycaprolactone (PCL) Dispersed in Adhesive Resin

A dispersion of PCL in an adhesive resin (Example 4) was prepared by combining Resin B (95.3 wt.-%) and TONE P767 (4.7 wt.-%) and mixing in a Speed Mixer (DAC-150-FVZ) operating at 3060 rpm for 4×30 seconds.

Example 5

PCL and ITO Dispersed in Adhesive Resin

A dispersion of PCL and ITO in an adhesive resin was prepared by combining Resin B (92.1 wt.-%), TONE P767 (5.0 wt.-%) and TRB SH 7080 (2.9 wt.-%) and mixing in a Speed Mixer (DAC-150-FVZ) operating at 3060 rpm for 4×30 seconds to provide a dispersion (Example 5) with a 1.2 wt.-% effective concentration of ITO.

Example 6

ITO Dispersed in Adhesive Composite

A dispersion of ITO in a filled adhesive was prepared by combining APC PLUS orthodontic adhesive (97.5 wt.-%) and TRB SH 7080 (2.5 wt.-%) and mixing in a Speed Mixer (DAC-150-FVZ) operating at 3000 rpm for 4×30 seconds to provide a dispersion (Example 6) with a 1.0 wt.-% effective concentration of ITO.

Example 7

PCL and ITO Dispersed in Adhesive Composite

A dispersion of PCL and ITO in a filled adhesive was prepared by combining APC PLUS orthodontic adhesive (95.0 wt.-%), TONE P767 (2.5 wt.-%) and TRB SH 7080 (2.5 wt.-%) and mixing in a Speed Mixer (DAC-150-FVZ) operating at 3000 rpm for 4×30 seconds to provide a dispersion (Example 7) with a 1.0 wt.-% effective concentration of ITO.

Example 8

Bracket Containing Successive Layers of Adhesive and ITO

A CLARITY bracket (3M Unitek) was silane treated as described in Evaluation D and coated with APC PLUS orthodontic adhesive (3M Unitek). The exposed adhesive end of the coated bracket was then stamped into TRB SH 7080 paste to provide a layer of ITO-containing material. By "stamped" is meant that the bracket was dipped into the low viscosity paste to produce a thin layer of the paste on the outer surface of the adhesive-coated bracket. The coated bracket was stored with the coated layer facing upwards and was evaluated immediately for bond strength.

Example 9

Bracket Containing Successive Layers of Adhesive, PCL, and ITO

A CLARITY bracket (3M Unitek) was silane treated as described in Evaluation D and coated with APC PLUS orthodontic adhesive (3M Unitek). The exposed adhesive end of the coated bracket was then sequentially stamped (as generally described in Example 8) into TONE P767 powder and TRB SH 7080 paste to provide sequential layers of PCL-containing material and ITO-containing material. The PCL and ITO layers were designed to be thin compared to the APC PLUS adhesive layer so as to influence fracture away from the bracket-adhesive interface, closer to the tooth for easier clean-up.

Evaluation A

Thermographic Analysis of ITO-Containing Cured Adhesive Compositions (Examples 2 and 3)

Cured disk samples of Examples 2 and 3 (ITO dispersions in adhesive resins) and a cured sample of Resin B without added ingredients (CONTROL) were irradiated with a 75 W QTH white light gun (Litema Astral Dental, Baden-Baden, Germany) with its IR reflecting filter removed. The light gun was held 5.5 mm from the top of the cured disks and a thermal imaging camera (TVS-8502, Avio, Japan) was held about 30 cm from the disks. An image was recorded approximately every 5 seconds, and the apparent temperatures plotted versus time. The measured maximum temperatures of the cured disk samples were both about 250° C., whereas the measured maximum temperature of the Resin B CONTROL was about 50° C. The maximum temperatures of all 3 samples were reached in 10-15 seconds. Therefore, it was demonstrated that a cured dental adhesive containing ITO could be heated rapidly to high temperatures with near infrared (NIR) radiation.

Evaluation B

Thermographic Analysis of ITO-Containing Cured Adhesive Composition (Example 2) on Ceramic Brackets A sample of Example 2 (ITO dispersion in Resin B) and a sample of Resin B without added ingredients (CONTROL) were used to adhere orthodontic brackets to glass slides according to the following procedure:

Window glass slides (3-mm thick×2.5-cm wide×10-cm long) were cleaned with methanol just prior to use. Approximately 10 mg of the adhesive test sample was placed on the non-fluorescent side of the cleaned slide as a single drop. A TRANSCEND 6000 ceramic bracket (3M Unitek, Monrovia, Calif.) was placed into the drop of adhesive formulation and bonding was carried out by irradiation through the glass slide using a medium pressure Hg spot cure lamp (100 W, Super Spot Max, Lesco, Torrance, Calif.) for 50 seconds.

Immediately after bonding, both brackets were sheared off the glass slides using an Instron R5500 universal testing machine fitted with an Instron Model 2511-111 500-N load cell. The brackets were collected and excess adhesive around the corners of the brackets was chipped away carefully leaving only the hardened adhesive at the base of the brackets. The brackets/hardened adhesives were then heated with NIR radiation as follows.

The brackets were held in an aluminum foil covered white card paper frame with the 75 W QTH Litema Astral Dental Light gun (with its IR reflecting filter removed) held 1 mm away from the top of the bracket on one side of the card paper frame. An Avio thermal imaging camera (TVS-8502 with a close focusing lens) was held approximately 7.5 cm from the base of the bracket at an angle away from the normal to avoid accidental direct radiation from the light gun. The recorded temperature was an apparent temperature assuming that the emissivity of the sample was unity. The temperature rise in the adhesive at the base of the bracket was monitored after the light gun was activated. An image was recorded approximately every 5 seconds. The temperature of the adhesive at the bracket base was plotted versus time and showed that the hardened Example 2 adhesive (with ITO) reached a temperature of about 140° C. after 20 seconds, whereas the CONTROL adhesive (without ITO) reached only about 60° C. after 20 seconds.

These data indicate that it is possible to rapidly heat up a hardened adhesive through the bracket to the $T_m$ of a semicrystalline polymer such as PCL in the presence of ITO. This localized heating will cause melting and subsequent debonding at slightly above the $T_m$ of the semicrystalline polymer. Furthermore, the use of a QTH source that is not tuned to the absorption spectrum of the ITO suggests that it may be possible to use other energy sources such as NIR LEDs or laser diodes that are tuned to the absorption of the NIR receptor.

Evaluation C

Bond Strength Evaluations of PCL- and PCL/ITO-Containing Cured Adhesive Compositions (Examples 4 and 5)

Debonding of Brackets from Glass Surfaces

Samples of Example 4 (PCL dispersion in Resin B) and Example 5 (PCL and ITO dispersion in Resin B) were used to adhere orthodontic brackets to glass slides as described in Evaluation B. Ten brackets were adhered with each adhesive.

Shear bond strengths were determined using the Shear Bond Strength on Glass Test Method A described herein and included irradiation with the 75 W QTH Litema Astral Dental Light gun (with its dichromic mirror removed). The results are provided in Table 2 and showed that debonding was greatly facilitated (i.e., lower bond strengths) with the presence of the NIR absorber ITO. The estimated temperatures of the samples exposed for 20 seconds to the NIR radiation was <60° C. and >100° C. for Example 4 and Example 5, respectively.

TABLE 2

Debonding of Ceramic Brackets from Glass Surface. Shear Bond Strength (MPa) after 20-Second Exposure to NIR Radiation.

| Run | Adhesive Example 4 (PCL Additive) | Adhesive Example 5 (PCL + ITO Additives) |
|---|---|---|
| 1 | 5.74 | 3.70 |
| 2 | 4.90 | 1.64 |
| 3 | 4.59 | 2.60 |
| 4 | 4.85 | 2.73 |
| 5 | 4.98 | 2.51 |
| 6 | 4.14 | 1.85 |
| 7 | 3.49 | 2.56 |
| 8 | 4.19 | 1.41 |
| 9 | 4.96 | 1.84 |
| 10 | 5.91 | 2.07 |
| Average: | 4.77 | 2.29 |

The evaluation was repeated with a new set of cured adhesive samples to determine the effect of aging on adhesion. The adhered-to-glass brackets were maintained at room temperature for 2.5 days under room lights before being debonded as described above. The results are provided in Table 3 and showed again that debonding was greatly facilitated with the presence of the NIR absorber ITO. These data showed more variance than in the above evaluation, but the average values are similar. The lower bond strengths for the ITO-containing samples are due to the much higher temperatures resulting from NIR irradiation through the brackets, in contrast to the samples that did not contain ITO.

TABLE 3

Debonding of Ceramic Brackets from Glass Surface after Ageing for 2.5 Days at Room Temperature. Shear Bond Strength (MPa) after 20-Second Exposure to NIR Radiation.

| Run | Adhesive Example 4 (PCL Additive) | Adhesive Example 5 (PCL + ITO Additives) |
|---|---|---|
| 1 | 4.55 | 2.72 |
| 2 | 5.96 | 2.50 |
| 3 | 6.28 | 1.89 |
| 4 | 3.53 | 0.92 |
| 5 | 3.17 | 1.54 |
| 6 | 5.02 | 1.85 |
| 7 | 5.60 | 2.20 |
| 8 | 2.54 | 1.61 |
| 9 | 6.10 | 1.70 |
| 10 | 4.84 | Not Tested |
| Average: | 4.76 | 1.88 |

Evaluation D

Bonded Strength Evaluations of ITO- and PCL/ITO-Containing Cured Adhesive Compositions (Examples 6 and 7)

Debonding of CLARITY Brackets from Bovine Teeth Surfaces

Samples of Example 6 (ITO dispersion in APC PLUS Adhesive), Example 7 (PCL and ITO dispersion in APC PLUS Adhesive), and APC PLUS Adhesive without additives (CONTROL) were used to adhere orthodontic brackets to bovine teeth. Five brackets were adhered with each adhesive.

Shear bond strengths using silane-treated CLARITY Brackets adhered to bovine teeth were determined using the Shear Bond Strength on Teeth Test Method B described herein and included NIR irradiation with the ORTHOLUX XT light source (3M Unitek) with its dichromic mirror removed. Additionally, bond strengths of the Example 6, Example 7, and CONTROL samples were run at about room temperature by the same Test Method, except that the NIR irradiation was omitted. The results are provided in Table 4 and showed a trend towards lower bond strengths with the presence of the NIR absorber ITO, and a further a trend towards lower bond strengths with the added presence of the PCL.

TABLE 4

Debonding of CLARITY Brackets from Bovine Teeth Surfaces. Shear Bond Strength (MPa) after 60-Second Exposure to NIR Radiation or No Exposure to NIR Radiation.

| | CONTROL Adhesive | Adhesive Example 6 (ITO Additive) | | Adhesive Example 7 (PCL + ITO Additives) | |
|---|---|---|---|---|---|
| Run | No NIR | No NIR | NIR | No NIR | NIR |
| 1 | 37.1 | 13.5 | 22.4 | 9.8 | 5.3 |

TABLE 4-continued

Debonding of CLARITY Brackets from Bovine Teeth Surfaces. Shear Bond Strength (MPa) after 60-Second Exposure to NIR Radiation or No Exposure to NIR Radiation.

| | CONTROL Adhesive | Adhesive Example 6 (ITO Additive) | | Adhesive Example 7 (PCL + ITO Additives) | |
|---|---|---|---|---|---|
| Run | No NIR | No NIR | NIR | No NIR | NIR |
| 2 | 18.8 | 18.8 | 10.2 | 16.3 | 9.4 |
| 3 | 15.1 | 20.8 | 8.2 | 16.7 | 10.6 |
| 4 | 28.2 | 17.5 | 16.7 | 11.0 | 9.8 |
| 5 | 28.6 | 13.9 | 22.8 | 17.1 | 13.1 |
| Average: | 25.5 | 16.9 | 16.1 | 14.2 | 9.6 |

Evaluation E

Bond Strength Evaluations of Cured Adhesive Compositions Containing Layers of ITO or PCL/ITO (Examples 8 and 9)

Debonding of CLARITY Brackets from Bovine Teeth Surfaces

APC PLUS Adhesive-coated silane-treated CLARITY brackets were prepared as described in Evaluation D (and the Shear Bond Strength on Teeth Test Method B) and then stamped into TRB SH 7080 paste to form a layer of ITO (Example 8) or into TONE P767 powder followed by TRB SH 7080 paste (Example 9) to form layers of PCL and ITO. The resulting layered brackets were allowed to stand for 24 hours at 37° C. and then were debonded as described in Evaluation D (and the Shear Bond Strength on Teeth Test Method B). It is noted that the layering with PCL was found to be difficult, likely due to the relatively large particle size, and as a result several PCL-layered samples failed during the bonding process.

The results are provided in Table 5 and showed that it may be possible to induce selective failure at an interface by layering with ITO and/or PCL materials. The presence of ITO only at the interface would be advantageous from the standpoint of preventing the generation of excess thermal mass.

TABLE 5

Debonding of CLARITY Brackets from Bovine Teeth Surfaces. Shear Bond Strength (MPa) after 60-Second Exposure to NIR Radiation or No Exposure to NIR Radiation.

| | Adhesive Example 8 (ITO Layer) | | Adhesive Example 9 (PCL + ITO Layers) | |
|---|---|---|---|---|
| Run | No NIR | NIR | No NIR | NIR |
| 1 | 17.1 | 19.2 | 14.3 | 5.7 |
| 2 | 13.5 | 17.5 | 2.0 | 3.7 |
| 3 | 11.8 | 6.1 | 16.3 | Not Tested |
| 4 | 40.0 | 2.9 | 15.9 | Not Tested |
| 5 | 20.8 | 5.7 | Not Tested | Not Tested |
| Average: | 20.6 | 10.3 | 12.1 | 4.7 |

Example 10 and Comparative Example 1 (CE-1)

PCL Fibers Layered on Cured Adhesive

One drop (approximately 10 mg) of adhesive (Resin C; HEMA—89.6 wt %, bisGMA—9.5 wt % and IRGACURE 819—0.9%) was placed on each of two ITO-coated glass slides (resistivity of about 600 ohms/square; available from Optera Inc., Holland, Mich.) with or without a deposit of PCL fibers. (See Starting Material Preparations.) The adhesive remained as a bead on the surface of the slide without PCL fibers, but immediately wet the slide with deposited PCL fibers. In both cases, another drop of adhesive was added to the prior drop, followed by placement of an orthodontic bracket (TRANSCEND 6000, 3M Unitek) to the adhesive drops on each of the slides. There was considerable wetting of the PCL fibers by this procedure.

The brackets were cured and adhered to the slides by irradiation for 30 seconds with a Super Spot Max fiber optic 100 W Hg—Xe light source (Lesco, Torrance, Calif.) and held 39 mm from the brackets. The resulting bracket assemblies were designated Example 10 (with PCL fibers) and Comparative Example 1 (CE-1) (without PCL fibers).

Example 11 and Comparative Example 2 (CE-2)

PCL Fibers Layered on Cured Adhesive

Example 11 (with PCL fibers) and Comparative Example 2 (CE-2) (without PCL fibers) were prepared as described for Example 10 and CE-1, except that the initial drop of Resin C was immediately followed by placement of the bracket, such that the adhesive did not have time to spread across the PCL surface and thus another drop of adhesive was not required or used. The brackets were cured and adhered to the slides as described for Example 10.

Evaluation F

Bond Strength Evaluations of Cured Adhesive Compositions Layered on PCL Fibers (Examples 10 and 11)

Debonding of Brackets (TRANSCEND 6000) from ITO-Treated Glass Surfaces

A 1000-g weight was hung from the brackets while simultaneously heating the back of the glass slide with a 250-Watt IR lamp (General Electric) operating at full power. The time to failure as well as the temperature at failure was recorded. The failure mode was also recorded for all brackets. The distance from the lamp to the back of the glass slide was 5 cm. Resulting data including Fiber Spinning Time (reflecting the quantity of PCL fibers on the glass slides), Trans (%) at 550 nm (measured on a Hewlett Packard 8452A Spectrophotometer interfaced with a PC running HP UV-JVis ChemStation software), Time of Failure, Temperature at Failure, and Failure Mode are provided in Table 6.

TABLE 6

Results for Examples 10-11 and Comparative Examples 1-2 (CE-1 and CE-2)

| Example/Run | Fiber Spinning Time | Trans (%) at 550 nm | Time of Failure (min:sec) | Temp. (° C.) at Failure | Failure mode |
|---|---|---|---|---|---|
| CE-1/Run 1 | Control | 79.2 | 8:45 | 130 | Adhesive Failure at glass surface |
| CE-1/Run 2 | Control | 79.4 | 10:00 | 121 | Adhesive Failure at glass surface |
| 10/Run 3 | 5 sec | 39.6 | 5:44 | 119 | Adhesive Failure at glass surface |
| 10/Run 4 | 5 sec | 41.9 | 1:43 | 84 | Adhesive Failure at glass surface |
| 10/Run 5 | 10 sec | 23.2 | 3:49 | 116 | Adhesive Failure at glass surface |
| 10/Run 6 | 10 sec | 22.5 | 2:43 | 112 | Adhesive Failure at glass surface |
| 10/Run 7 | 15 sec | 16.1 | 5:27 | 133 | Adhesive Failure at glass surface |
| 10/Run 8 | 15 sec | 13.4 | 7:04 | 142 | Adhesive Failure at glass surface |
| CE-2/Run 9 | Control | 79.7 | 2:18 | 100 | Adhesive Failure at glass surface |
| CE-2/Run 10 | Control | 79.5 | 3:22 | 113 | Adhesive Failure at glass surface |
| CE-2/Run 11 | Control | 80 | 3:15 | 100 | Cohesive failure 70% left on glass |
| 11/Run 12 | 5 sec | 51.2 | 1:27 | 81 | Adhesive Failure at glass surface |
| 11/Run 13 | 5 sec | 45.5 | 1:18 | 96 | Adhesive Failure at glass surface |
| 11/Run 14 | 5 sec | 55.5 | 0:45 | 60 | Adhesive Failure at glass surface |
| 11/Run 15 | 10 sec | 26.9 | 0:52 | 69 | Adhesive Failure at glass surface |
| 11/Run 16 | 10 sec | 23.9 | 1:27 | 81 | Adhesive Failure at bracket |
| 11/Run 17 | 10 sec | 22.6 | 1:05 | 75 | Adhesive Failure at glass surface |
| 11/Run 18 | 15 sec | 18.5 | 0:44 | 69 | Adhesive Failure at glass surface |
| 11/Run 19 | 15 sec | 17.5 | 1:07 | 87 | Adhesive Failure at glass surface |
| 11/Run 20 | 15 sec | 20.2 | 1:12 | 91 | Adhesive Failure at glass surface |
| 11/Run 21 | 20 sec | 15.4 | 1:33 | 90 | Adhesive Failure at glass surface |
| 11/Run 22 | 20 sec | 16.4 | 1:11 | 91 | Adhesive Failure at glass surface |
| 11/Run 23 | 20 sec | 17.1 | 1:23 | 81 | Adhesive Failure at glass surface |

Visible melting of the PCL was evident on heating the brackets. The PCL appeared to turn clear from hazy white on melting. Bracket failure was observed to be sudden with no visual evidence of creep. It should be pointed out that the temperatures at failure indicated in Table 6 were measured at a short distance above the bracket (closer to the lamp) and may not be indicative of the temperatures at the PCL-bracket interface.

While the results for Example 10 show loss in adhesion as expected in the presence of PCL, there is no clear pattern that shows progressive reduction of time to failure upon increasing the PCL fiber concentration on the glass slide. There is also significant variance in the data.

The results for Example 11 (that avoids the use of excess adhesive) show less variance and demonstrate a consistent pattern of adhesion loss upon melting of the PCL layer. The measured temperature at failure appears to be reasonable given that the melting point of PCL (TONE P767) is in the 57° C. to 64° C. region depending on the thermal history of the material.

The Example 11 data are consistent with the concept of debonding by the placement of fibers (preferably nanofibers) of thermoplastic materials at interfaces. It appears from Table 6 that even a very sparse layer of PCL fibers (e.g., see Example 11/Runs 12-13; "5 seconds" Fiber Spinning Time) is sufficient to affect debonding times. These results suggest that even slight modifications in the bonding interface can bring about reliable and efficient debonding. The use of thermoplastics (e.g., PCL fibers) at the tooth-adhesive interface should allow on demand debonding with the application of heat.

Example 12A-B and Comparative Example 3

PCL Fibers Containing ITO Nanoparticles and Layered on Cured Adhesive

Figure 10A:
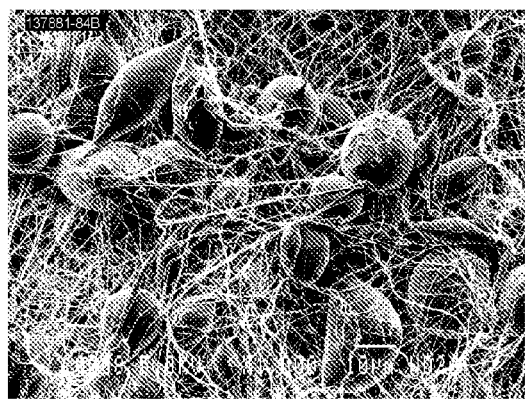
FIG. 10a illustrates scanning electron micrographs of poly (caprolactone) (PCL) nanofibers including indium-tin oxide (ITO) particles.
Figure 10B:
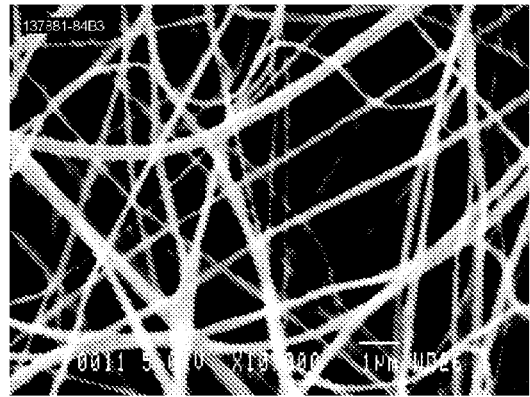

In a glass vial was placed a sample (10.0 g) of Electrospinning Solution A (20% TONE P767 in MEK) and TRB SH 7080 (0.30 g). The mixture was hand stirred with a wooden stick to give a cloudy, blue solution that was transferred to a 60-ml disposable syringe to perform the electrospinning. The electrospinning was performed as described in Starting Material Preparations with the flow rate set at 10.2 ml/hour. Transmission measurements were used to monitor the density of fibers on the glass slides to help obtain similar densities to the ones that did not contain the ITO particles. Scanning electron microscopy of fibers prepared using these conditions show a random mat of mostly sub-micron fibers with a few fibers having diameters up to 10 microns. Large beads are also present of a few of the fibers as shown in the micrographs in FIGS. 10a-b. The PCL plus ITO fiber mats were designated Example 12A. Corresponding PCL (without ITO) fiber mats were also prepared.

One drop (approximately 10 mg) of adhesive (Resin D; See Starting Material Preparations) was placed on each of two glass slides with either a PCL/ITO fiber mat (Example 12A) or a PCL only fiber mat. Immediately, an orthodontic bracket (TRANSCEND 6000, 3M Unitek) was placed onto each of the adhesive drops on each of the glass slides. The brackets were immediately cured and adhered to the slides by irradiation for 20 seconds with a Curing Light 2500 (3M ESPE), positioned such that the optical fiber tip rested lightly on the bracket. The resulting bracket assemblies were designated Example 12B (with PCL/ITO fibers) and Comparative Example 3 (CE-3) (with PCL only fibers).

Example 13A-B and Comparative Example 4

PPC Fibers Containing ITO Nanoparticles and Layered on Cured Adhesive

In a glass vial was placed a sample (10 g) of Electrospinning Solution B (20%; 10 g QPAC-40 in MEK), TRB SH 7080 (0.60 g), and DBU (0.09 g). (Polycarbonates have been shown to have base sensitivity; therefore, to effect a lower degradation temperature, diazabicyclo[5.4.0]undec-7-ene (DBU) was added to the spinning formulation at the 1% level. For the formulations containing the ITO nanoparticles, the QPAC-40 solution and the TRB SH 7080 were combined an a glass vial and mixed by hand stirring before the DBU was added and stirred in by hand.)

Figure 11A:
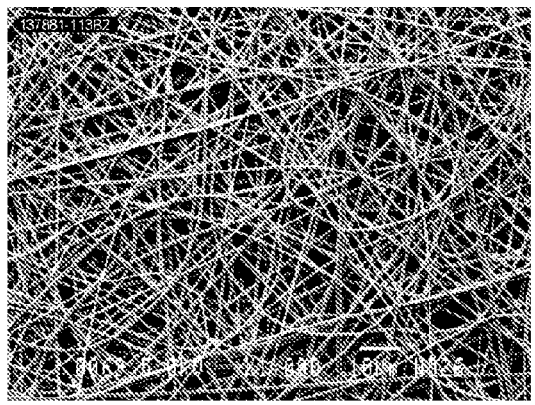
FIG. 11a illustrates scanning electron micrographs of poly (propylene carbonate), (PPC) nanofibers.
Figure 11B:
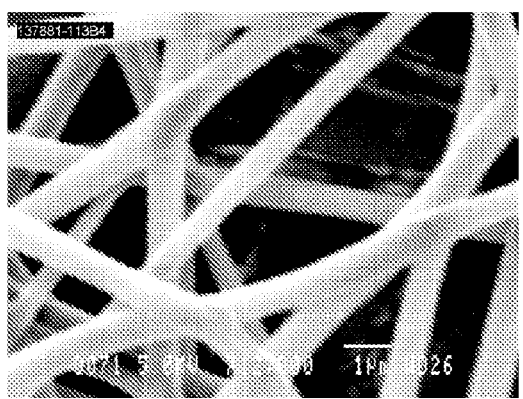

The electrospinning was performed as described above (See Starting Material Preparations) with the flow rate set at 2.0 ml/hour and a time duration of approximately 120 seconds. Transmission measurements were used to monitor the density of fibers on the glass slides and many required additional electrospinning to give transmittances close to what was seen on the control slides (without ITO particles). During the electrospinning process, liquid droplets were depositing on the aluminum ground plane and the glass slides; therefore, a new spinning formulation was prepared that contained Electrospinning Solution B (5 g, 20% QPAC-40 in MEK), TRB SH 7080 (0.30 g), and DBU (0.05 g). The last two slides (Example 14/Runs 23-24) were coated with this new spinning formulation. Scanning electron microscopy (FIGS. 11a-b) of fibers prepared using these conditions showed a mat of fibers that have a very uniform fiber diameter distribution between 600 nm and 1000 nm. The PPC/DBU plus ITO fiber mats were designated Example 13A. Corresponding PPC/DBU (without ITO) fiber mats were also prepared.

One drop (approximately 10 mg) of adhesive (Resin D; See Starting Material Preparations) was placed on each of glass slides with either a PPC/DBU/ITO fiber mat (Example 13A) or a PPC/DBU only fiber mat. Immediately, an orthodontic bracket (TRANSCEND 6000, 3M Unitek) was placed onto each of the adhesive drops on each of the glass slides. The brackets were immediately cured and adhered to the slides by irradiation for 20 seconds with a Curing Light 2500 (3M ESPE), positioned such that the optical fiber tip rested lightly on the bracket. The resulting bracket assemblies were designated Example 13B (with PPC/DBU/ITO fibers) and Comparative Example 4 (CE-4) (with PCL/DBU only fibers).

Example 14A-B and Comparative Example 5

PCL Fibers Containing NIR (Near IR) Absorbing Dye and Layered on Cured Adhesive

Figure 12A:
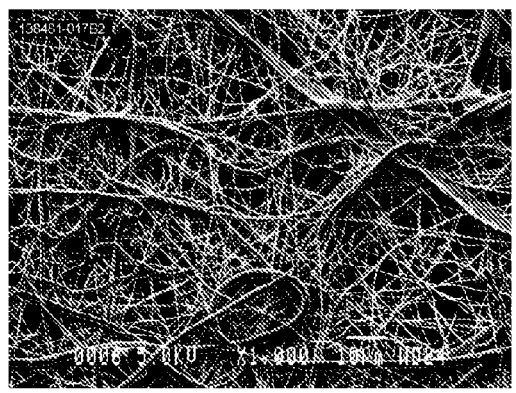
FIG. 12a illustrates scanning electron micrographs of poly (caprolactone) (PCL) nanofibers including a near infrared (NIR) absorber dye.
Figure 12B:
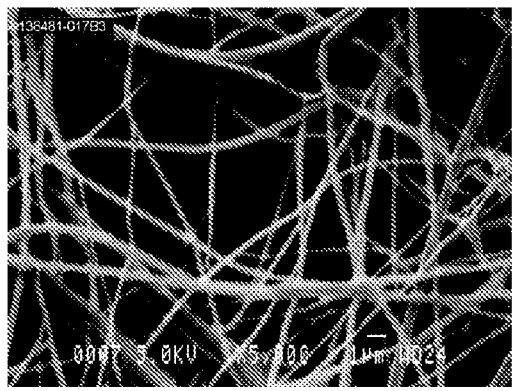

In a glass vial was placed a sample (10.0 g) of Electrospinning Solution A (20% TONE P767 in MEK) and EPOLIGHT 2057 dye (0.033 g). The mixture was hand stirred with a wooden stick to give a green solution that was transferred to a 60-ml disposable syringe to perform the electrospinning. The electrospinning was performed as described in Starting Material Preparations with the flow rate set at 2.0 ml/hour. Transmission measurements were used to monitor the density of fibers on the glass slides to help obtain similar densities to the ones that did not contain the dye. Scanning electron microscopy of fibers prepared using these conditions show a random mat of mostly sub-micron fibers with a few fibers (<5%) having diameters up to 10 microns. Large beads are also present of a few of the fibers as shown in the micrographs in FIGS. 12a-b. The PCL plus dye fiber mats were designated Example 14A. Corresponding PCL (without dye) fiber mats were also prepared.

Adhesive (Resin D) was used to adhere brackets to glass slides as described for Example 12B. The resulting bracket assemblies were designated Example 14B (with PCL/Dye fibers) and Comparative Example 5 (CE-5) (with PCL only fibers).

Evaluation G

Bond Strength Evaluations of Cured Adhesive Compositions Layered on PCL/ITO, PPC/DBU/ITO, and PCL/Dye Fiber Mats (Examples 12B, 13B and 14B)

Debonding of Brackets (TRANSCEND 6000) from Glass Surfaces

A 1500-g weight was hung from the brackets while simultaneously irradiating the back of the glass slide with a 75 W QTH white light gun (Litema Astral Dental Light gun) with its IR reflecting filter removed. The light gun was positioned such that the end of the optical fiber was touching the glass slide, directly behind the adhered bracket. The time to failure as well as the temperature at failure was recorded. The failure mode was also recorded for all brackets. Resulting data including Transmittance (%) at 550 nm (measured on a Hewlett Packard 8452A Spectrophotometer interfaced with a PC running HP UV-Vis ChemStation software), Time of Failure, and Failure Mode are provided in Table 7.

TABLE 7

Results for Examples 12B, 13B, 14B and Comparative Examples 3-5 (CE-3, CE-4 and CE-5)

| Example | Run | Trans (%) at 550 nm | Time of Failure (min:sec) | Failure Mode |
|---|---|---|---|---|
| CE-3 | 1 | 1.005 | >3:00 | None |
| | 2 | 1.739 | >3:00 | None |
| | 3 | 1.976 | 2:06 | Adhesive Failure at glass surface |
| | 4 | 1.106 | 2:12 | Adhesive Failure at glass surface |
| | 5 | 2.481 | >3:00 | None |
| 12B | 6 | 4.02 | 1:10 | Adhesive Failure at glass surface |
| | 7 | 1.697 | 0:52 | Adhesive Failure at glass surface |
| | 8 | 3.447 | 1:25 | Adhesive Failure at glass surface |
| | 9 | 0.679 | 0:55 | Adhesive Failure at glass surface |
| | 10 | 0.713 | 1:15 | Adhesive Failure at glass surface |
| CE-4 | 11 | 4.284 | >3:00 | None |
| | 12 | 2.086 | 2:50 | Mixed |
| | 13 | 2.118 | >3:00 | None |
| | 14 | 5.135 | >3:00 | None |
| | 15 | 5.495 | >3:00 | None |
| 13B | 16 | 2.418 | 1:28 | Adhesive Failure at glass surface |
| | 17 | 4.551 | 0:17 | Mixed |
| | 18 | 5.549 | 0:22 | Adhesive Failure at glass surface |
| | 19 | 4.596 | 1:33 | Adhesive Failure at glass surface |
| CE-5 | 20 | 4.634 | >3:00 | None |
| 14B | 21 | 4.251 | 1:36 | Adhesive Failure at glass surface |
| | 22 | 4.122 | 0:04 | Adhesive Failure at glass surface |
| | 23 | 3.838 | 0:58 | Adhesive Failure at glass surface |
| | 24 | 3.889 | 1:39 | Adhesive Failure at glass surface |

Visible melting of the PCL fibers (Examples 12B and CE-3) was evident after irradiating the brackets for 20 seconds. The PCL appeared to turn clear from hazy white on melting. Bracket failure was observed to be sudden with no visual evidence of creep. The data from Table 7 show that bonded brackets with a fiber mat of only PCL (CE-3) show little or no changes in adhesive strength when irradiated with the 75-Watt QTH bulb; whereas, a significant decrease in adhesive strength was observed when samples having the ITO-containing PCL nanofibers (Example 12B) were irradiated.

Visible melting and degradation of the PPC fibers (Examples 13B and CE-4) were evident after irradiating the brackets for 30 seconds. The cloudy fiber mat changed to a clear ring around the bound bracket. Bracket failure was observed to be sudden with no visual evidence of creep. One of the control samples (Run 12) showed a mixed failure mode; meaning, that complete adhesive failure at the adhesive/glass interface was observed directly behind the bracket, but that cohesive failure of the adhesive was observed at the top edge of the bracket with a sharp break of the adhesive at the edge of the bracket. Some adhesive was left on the glass substrate above the bracket, but the adhesive below the bracket was removed. The data from Table 7 show that bonded brackets with a fiber mat of only PPC/DBU (CE-4) show little or no changes in adhesive strength when irradiated with the 75-Watt QTH bulb; whereas, a significant decrease in adhesive strength was observed when samples having the ITO-containing PPC/DBU nanofibers (Example 13B) were irradiated.

Visible melting of the PCL fibers (Examples 14B and CE-5) was evident after irradiating the brackets for 20 seconds. The PCL appeared to turn clear, from hazy white, on melting. Bracket failure was observed to be sudden with no visual evidence of creep. The data from Table 7 show a decrease in adhesive strength when the PCL nanofibers containing the EPOLIGHT dye were irradiated with the 75-Watt QTH bulb.

Example 15

BHA/HEMA-IEM Particles and ITO Dispersed in Adhesive Resin

A dispersion of a thermally responsive material and ITO in an adhesive resin was prepared by combining Resin A (71.2 wt.-%), BHA/HEMA-IEM Particles (24.3 wt.-%; see Starting Materials Preparation) and TRB SH 7080 (4.5 wt.-%) and mixing in a Speed Mixer (Model DAC-150-FVZ) at 3000 rpm for 60 seconds×3 cycles to provide a dispersion (Example 15) with a 1.8 wt.-% effective concentration of ITO.

Evaluation H

Bond Strength Evaluations of BHA/HEMA-IEM Particles-Containing Cured Adhesive Composition (Examples 15)

Debonding of TRANSCEND 6000 Brackets from Bovine Teeth Surfaces

Samples of Example 15 were used to adhere orthodontic brackets to bovine teeth. Five brackets were adhered for each of the two procedures utilized.

Shear bond strengths using TRANSCEND 6000 Brackets adhered to bovine teeth were determined using generally the Shear Bond Strength on Teeth Test Method A described herein, except that a dental halogen lamp Model 2500 (3M ESPE) was used for 20 seconds to adhere the brackets to the teeth. For Procedure A, the brackets were shear debonded on the Instron R5500 as described in Teeth Test Method A. For Procedure B, the brackets were loaded onto the Instron instrument and irradiated for 10 seconds with a Cuda fiber optic light source (Model I-100, Sunoptic Technologies, Jacksonville, Fla.) that was fitted with a quartz-tungsten-halogen lamp possessing a gold-coated ellipsoidal reflector (Model L6408-G, Gilway Scientific, Woburn, Mass.) and a NIR transmitting optical fiber (Newport Oriel, Stratford, Conn.). The Instron loadframe was activated immediately following the 10-second NIR exposure. The results are provided in Table 8 and show the significantly reduced bond strength of samples following the 10-second NIR exposure as compared to the samples without NIR exposure.

TABLE 8

Debonding of TRANSCEND Brackets from Bovine Teeth Surface.
Shear Bond Strength (MPa)

| Run | Example 15 Procedure A (No NIR) | Example 15 Procedure B (10-Second NIR) |
| --- | --- | --- |
| 1 | 8.39 | 3.20 |
| 2 | 9.83 | 4.45 |
| 3 | 9.85 | 3.72 |
| 4 | 6.86 | 3.56 |
| 5 | 6.98 | 2.32 |
| Average: | 8.38 | 3.45 |

Example 16

Photobonding and Photothermal Debonding on Teeth Using an Adhesive Containing t-BOCDMA/HEMA/IRGACURE/Sulfonium Salt/NIR-Absorber In order to demonstrate the photobonding and photothermal debonding properties of adhesives containing t-BOCDMA, an adhesive coating containing t-BOCDMA was prepared and photochemically cured to adhere orthodontic brackets to bovine teeth surfaces. The adhered brackets were subjected to sequential UVA light irradiation and heat (generated by white-light irradiation of the near infrared (NIR)-absorber present in the adhesive), and shear bond strengths determined. These procedures were carried out as follows.

An adhesive formulation (Example 16) consisting of HEMA (51.1%), t-BOCDMA (5.7%), $Ar_3S^+PF_6^-$ (5.4% of a 50% solution in propylene carbonate), IRGACURE 819 (0.5%), TRB SH 7080 NIR-absorber (2.1%), and SO-E2 silica powder filler (35.2%) was prepared by mixing the components in a Branson Model 2510 ultrasonic bath (Branson, Danbury, Conn.) for 20 minutes.

Thirteen bovine teeth were potted in a poly(methyl methacrylate) base and were etched and primed using ADPER PROMPT L-Pop self-etching adhesive (3M ESPE, St. Paul, Minn.) for 30 seconds followed by blowing with a stream of air to remove excess adhesive. Approximately 10 mg (one drop) of the adhesive formulation was placed on a treated tooth surface. A TRANSCEND 6000 ceramic bracket (Part Nos. 59543-01, 3M Unitek) was carfdully placed into the drop of adhesive formulation and bonding was carried out by irradiating all 13 bracket samples with a Lesco Super Spot Max light source fitted with a 420-nm long pass filter (GG 420, Esco Products). Irradiation was carried out three times for 15 seconds with 30-second intervals.

For the debonding experiments, seven of the bonded brackets (Test Samples) were irradiated by exposure for 6×10 seconds to UVA light using the same LESCO Super Spot Max light source (but without the GG420 filter). There was a 30-second interval between each irradiation period for a given tooth to avoid overheating. Six of the bonded bracket samples (Controls) were irradiated by exposure for 6 cycles of 10 seconds each with 30-second intervals to the same LESCO Super Spot Max light source (fitted with the 420-nm long pass GG 420 filter, thus, to mimic the heat provided from the light source during the UVA activation step, but without UVA light). Seven of the bonded bracket samples were irradiated by exposure for 6 cycles of 10 seconds each with 30-second intervals to UVA light using the same LESCO Super Spot Max light source (but without the filter). Bond strengths were then determined according to the Shear Bond Strength on Teeth Test Method C described herein.

Results are shown in Table 9 for 6 Runs with no UV irradiation and 7 Runs with 60 seconds of UV irradiation plus an average result for each series of Runs.

TABLE 9

Debonding of Ceramic Brackets from Glass Surface.
Shear Data (MPa) at 100° C.

| Run | No UV | 60 sec UV |
| --- | --- | --- |
| 1 | 4.78 | 1.09 |
| 2 | 5.24 | 0.62 |
| 3 | 3.77 | 0.78 |
| 4 | 9.09 | 0.98 |
| 5 | 8.67 | 1.37 |
| 6 | 3.29 | 1.13 |
| 7 | — | 1.11 |
| Average: | 5.81 | 1.01 |

It is seen from the data in Table 9 that there is a significant failure at about 100° C. in adhesion of the bracket samples that had been irradiated with UVA light relative to the non-UVA-irradiated control samples.

Example 17

Photobonding and Photothermal Debonding on Teeth Using an Adhesive Containing CHDVEDMA/HEMA/IRGACURE/Sulfonium Salt/NIR-Absorber In order to demonstrate the photobonding and photothermal debonding properties of adhesives containing CHDVEDMA, a silica-filled orthodontic adhesive coating containing CHDVEDMA was prepared and photochemically cured to adhere orthodontic brackets to bovine teeth surfaces. The adhered brackets were subjected to sequential UVA light irradiation and heat (generated by white-light irradiation of the near infrared (NIR)-absorber present in the adhesive), and shear bond strengths determined. These procedures were carried out as follows.

A liquid adhesive composition (Example 17) of CHDVEDMA (26.5 wt.-%), HEMA (26.5 wt.-%), $Ar_3S^+ PF_6^-$ (3.3 wt.-%), IRGACURE 819 (0.6 wt.-%), SO-E2 Filler (39.9 wt.-%), and TRB SH 7080 (3.3 wt.-%) was prepared by mixing the combined components in a DAC-150 SpeedMixer (manufactured by Hauschild & Co, Hamm, Germany and distributed by FlackTek, Inc., Landrum, S.C.) at room temperature for 3×1 minutes.

Nine bovine teeth were potted in a poly(methyl methacrylate) base, dried with a stream of dry air, and were etched and primed using ADPER PROMPT L-Pop self-etching adhesive (3M ESPE, St. Paul, Minn.) for 10 seconds followed by blowing with a stream of air to remove excess adhesive. Approximately 10 mg of the orthodontic adhesive formulation was placed on a treated tooth surface. A TRANSCEND 6000 ceramic bracket (Part Nos. 59543-01, 3M Unitek) was carefully placed onto the adhesive formulation and bonding was carried out by irradiating all nine bracket samples with a Lesco Super Spot Max light source fitted with a 420-nm long pass filter (GG 420, Esco Products). Irradiation was carried out two times for 15 seconds with a 30-second interval.

For the debonding experiments, four of the bonded brackets (Test Samples) were irradiated by exposure for 6×10 seconds to UVA light using the same LESCO Super Spot Max light source (but without the filter). There was a 30-second interval between each irradiation period for a given tooth to avoid overheating. Five of the bonded bracket samples (Controls) were irradiated by exposure for 6×10 seconds to the same LESCO Super Spot Max light source (fitted with the 420-nm long pass GG 420 filter; thus, to mimic the heat provided from the light source during the UVA activation step, but without UVA light). As a result four bonded brackets were UV-activated and five bonded brackets were not. Bond strengths were then determined according to the Shear Bond Strength on Teeth Test Method C described herein.

Results are shown in Table 10 for 4-5 replicates at the two different levels of UVA irradiation (i.e., no UVA, and UVA exposure for 6×10 seconds) plus an average result for each level.

TABLE 10

Debonding of Ceramic Brackets from Teeth Surfaces.
Bond Strength (MPa) after about 100° C. Exposure

| Run | No UVA | 6 × 10 sec UVA |
|---|---|---|
| 1 | 5.58 | 2.51 |
| 2 | 5.36 | 2.59 |
| 3 | 3.82 | 3.71 |
| 4 | 7.67 | 3.85 |
| 5 | 6.94 | — |
| Average: | 5.87 | 3.16 |

It is seen from the data in Table 10 that there is a significant failure (after visible-light induced heating) in adhesion of the UVA-irradiated Test Brackets relative to the non-UVA-irradiated Control Brackets. The failure mode for all brackets (Control Brackets and Test Brackets) was cohesive.

Examples 18-19

RF Absorbing Magnetic Ceramic Powders and PCL Dispersed in Adhesive Resin

A composition of PCL, NiZn ferrite, and filler dispersed in an adhesive resin is prepared by combining Resin B (20 wt.-%), TONE P767 (5.0 wt.-%), Filler E (70.0 wt.-%), and NiZn ferrite powder (5.0 wt.-%) and mixing in a Speed Mixer (DAC-150-FVZ) operating at 3060 rpm for 4×30 seconds to provide a composition (Example 18).

A composition (Example 19) of PCL and Mg—Mn—Zn mixed ferrite in Resin B is prepared in the same manner as Example 18, except that Mg—Mn—Zn mixed ferrite is substituted for the NiZn ferrite.

Transcend 6000 brackets are bonded to prophyed bovine teeth potted in PMMA using Transbond SEP and the above compositions (Example 18 or Example 19) as the adhesive. The bonded brackets are stored in water at 37° C. for 24 hours and debonded on an Instron using the Shear Bond Strength on Teeth Test Method C with the following change: The Litema Astral light source is replaced with a RF source operating at 100 KHz. The bracket is irradiated with RF for 10 seconds and the Instron load frame is activated immediately following the RF irradiation. Control samples (identical to Examples 18 and 19, but without any ferrite in the compositions) are similarly debonded.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method for reducing the bond strength of an orthodontic appliance adhered to a tooth structure with a hardened dental composition comprising a radiation-to-heat converter, the method comprising irradiating the radiation-to-heat converter to reduce the bond strength, wherein the radiation-to-heat converter is selected from the group consisting of indium tin oxide, antimony tin oxide, and lanthanum hexaboride.

2. The method of claim 1 wherein the hardened dental composition is a hardened primer, and the orthodontic appliance is further adhered to a primed tooth structure with a hardened orthodontic adhesive.

3. The method of claim 2 further comprising removing the orthodontic appliance from the tooth structure.

4. The method of claim 3 wherein the hardened orthodontic adhesive is substantially retained on the removed orthodontic appliance.

5. The method of claim 1 wherein the radiation-to-heat converter is dissolved, dispersed, or suspended in the hardened dental composition.

6. The method of claim 1 wherein the radiation-to-heat converter is in the form of particles, powders, fibers, disks, plates, flakes, tubes, films, or combinations thereof.

7. The method of claim 1 wherein the radiation-to-heat converter is distributed uniformly throughout the hardened dental composition.

8. The method of claim 1 wherein the radiation-to-heat converter is concentrated in a portion of the hardened dental composition.

9. The method of claim 8 wherein the portion is near one surface of the hardened dental composition.

10. The method of claim 9 wherein the one surface is proximate the tooth structure.

11. The method of claim 1 wherein irradiating comprises heating at least a portion of the hardened dental composition to at least 42° C.

12. The method of claim 11 wherein the dental composition further comprises one or more of a thermally responsive additive; a thermally labile component comprising one or more thermally labile groups; and/or an acid-generating component and an acid-reactive component comprising one or more acid reactive groups.

* * * * *

UNITED STATES PATENT AND TRADEMARK OFFICE
CERTIFICATE OF CORRECTION

PATENT NO.        : 7,896,650 B2
APPLICATION NO.   : 11/275243
DATED             : March 1, 2011
INVENTOR(S)       : Joan V. Brennan It is certified that error appears in the above-identified patent and that said Letters Patent is hereby corrected as shown below:

Column 2
Line 6, Delete "applicances)" and insert -- appliances) --, therefor.

Column 5
Line 64, Delete "diimonium" and insert -- diammonium --, therefor.

Column 6
Line 27, Delete "squarilium" and insert -- squarylium --, therfeor.
Line 28, Delete "diimonium" and insert -- diammonium --, therefor.

Column 9
Line 7, Delete "hexacrylate," and insert -- hexaacrylate, --, therefor.

Column 16
Line 30, Delete "tetrafluoroboarate." and insert -- tetrafluoroborate. --, therefor.

Column 18
Line 32, Delete "unimodial" and insert -- unimodal --, therefor.
Line 32, Delete "polymodial" and insert -- polymodal --, therefor.

Column 23
Line 36, Delete "Comonents" and insert -- Components --, therefor.

Column 26
Line 2, Delete "Cinncinnati," and insert -- Cincinnati, --, therefor.
Line 3, Delete "microcystalline" and insert -- microcrystalline --, therefor.

Column 38
Line 39, Delete "Rutherforsd," and insert -- Rutherford, --, therefor.

Signed and Sealed this
Twenty-sixth Day of April, 2011

David J. Kappos
*Director of the United States Patent and Trademark Office*

CERTIFICATE OF CORRECTION (continued)
U.S. Pat. No. 7,896,650 B2

Column 42
Line 62, After "The" insert -- above --.

Column 45
Line 62, Delete "UV-JVis" and insert -- UV-JV is --, therefor.

Column 51
Line 62, Delete "cardfully" and insert -- carefully --, therefor.

Column 52
Line 10, Delete "filter," and insert -- filter; --, therefor.